United States Patent
Cohen et al.

(10) Patent No.: US 9,205,227 B2
(45) Date of Patent: *Dec. 8, 2015

(54) REMOTELY CONTROLLED CATHETER INSERTION SYSTEM

(76) Inventors: Todd J. Cohen, Port Washington, NY (US); Michael Eilenberg, Port Washington, NY (US)

( * ) Notice: Subject to any disclaimer, the term of this patent is extended or adjusted under 35 U.S.C. 154(b) by 199 days.

This patent is subject to a terminal disclaimer.

(21) Appl. No.: 13/461,463

(22) Filed: May 1, 2012

(65) Prior Publication Data

US 2012/0220931 A1 Aug. 30, 2012

Related U.S. Application Data

(62) Division of application No. 11/485,595, filed on Jul. 11, 2006, now Pat. No. 8,202,244.

(60) Provisional application No. 60/698,271, filed on Jul. 11, 2005.

(51) Int. Cl.
*A61M 25/092* (2006.01)
*A61M 25/01* (2006.01)
*A61B 19/00* (2006.01)

(52) U.S. Cl.
CPC ........ *A61M 25/0105* (2013.01); *A61B 19/2203* (2013.01); *A61B 2019/2211* (2013.01)

(58) Field of Classification Search
CPC .................. A61B 19/2203; A61B 2019/2211; A61M 25/0105; A61M 25/0108; A61M 25/0116; A61M 25/0133
USPC ............... 604/95.01; 600/104, 106, 111, 114, 600/118, 167, 147; 606/108
See application file for complete search history.

(56) References Cited

U.S. PATENT DOCUMENTS 4,549,538 A * 10/1985 Schadrack et al. ............ 606/104
4,721,123 A 1/1988 Cosentino et al.
(Continued)

FOREIGN PATENT DOCUMENTS

WO 2005087128 9/2005
WO 2007008967 A2 1/2007
WO 2009092059 A3 7/2009

OTHER PUBLICATIONS

WIPO, International Preliminary Report on Patentability; PCT/US2006/027024; Jan. 16, 2008; 8pgs.
(Continued)

*Primary Examiner* — Quynh-Nhu H Vu
(74) *Attorney, Agent, or Firm* — The Marbury Law Group, PLLC

(57) ABSTRACT

A remotely controlled insertion system for a medical device is described. The system comprises a robotic device and a remote control mechanism. The robotic device has a handle controller to receive and hold the control handle or proximal end of a medical device. The medical device is capable of moving in up to six ranges of motion. In one embodiment a first motor is connected through a drive screw to a handle controller to move the medical device forward and backward. A second motor is connected to drive wheels effective to rotate the medical device clockwise and counter-clockwise. A third motor drives a series of gears that are connected to one or more control members on the medical device, this being effective to deflect a tip of the medical device so that movement of the third motor causes such deflection. A control unit is connected to all three motors.

8 Claims, 15 Drawing Sheets

(56) References Cited

U.S. PATENT DOCUMENTS

| | | |
|---|---|---|
| 5,649,956 A | 7/1997 | Jensen et al. |
| 5,810,880 A | 9/1998 | Jensen et al. |
| 5,814,038 A | 9/1998 | Jensen et al. |
| 5,855,583 A | 1/1999 | Wang et al. |
| 5,951,461 A | 9/1999 | Nyo et al. |
| 6,007,550 A | 12/1999 | Wang et al. |
| 6,063,095 A | 5/2000 | Wang et al. |
| 6,080,181 A | 6/2000 | Jensen et al. |
| 6,096,004 A * | 8/2000 | Meglan et al. ............ 604/95.01 |
| 6,132,368 A | 10/2000 | Cooper |
| 6,171,234 B1 | 1/2001 | White et al. |
| 6,171,277 B1 | 1/2001 | Ponzi |
| 6,200,315 B1 * | 3/2001 | Gaiser et al. ................ 606/41 |
| 6,346,072 B1 | 2/2002 | Cooper |
| 6,398,755 B1 * | 6/2002 | Belef et al. ................ 604/95.01 |
| 6,413,264 B1 | 7/2002 | Jensen et al. |
| 6,445,984 B1 | 9/2002 | Kellogg |
| 6,461,372 B1 | 10/2002 | Jensen et al. |
| 6,527,782 B2 | 3/2003 | Hogg et al. |
| 6,620,174 B2 | 9/2003 | Jensen et al. |
| 6,726,675 B1 * | 4/2004 | Beyar ............................ 604/510 |
| 6,788,999 B2 | 9/2004 | Green |
| 6,850,817 B1 | 2/2005 | Green |
| 6,963,792 B1 | 11/2005 | Green |
| 6,974,465 B2 | 12/2005 | Belef et al. |
| 6,999,852 B2 | 2/2006 | Green |
| 7,006,895 B2 | 2/2006 | Green |
| 7,044,907 B2 * | 5/2006 | Belson ........................ 600/146 |
| 7,090,683 B2 | 8/2006 | Brock et al. |
| 7,118,582 B1 | 10/2006 | Wang et al. |
| 7,169,141 B2 | 1/2007 | Brock et al. |
| 7,204,844 B2 | 4/2007 | Jensen et al. |
| 7,214,230 B2 | 5/2007 | Brock et al. |
| 7,276,044 B2 | 10/2007 | Ferry et al. |
| 7,314,230 B2 | 1/2008 | Kumagai et al. |
| 7,331,967 B2 | 2/2008 | Lee et al. |
| 7,357,774 B2 | 4/2008 | Cooper |
| 7,371,210 B2 | 5/2008 | Brock et al. |
| 7,377,906 B2 | 5/2008 | Selkee |
| 7,537,570 B2 | 5/2009 | Kastelein |
| 7,630,752 B2 | 12/2009 | Viswanathan |
| 7,648,513 B2 | 1/2010 | Green et al. |
| 7,758,564 B2 | 7/2010 | Long et al. |
| 8,046,049 B2 | 10/2011 | Govari et al. |
| 8,202,244 B2 * | 6/2012 | Cohen et al. ................ 604/95.01 |
| 8,672,880 B2 * | 3/2014 | Cohen et al. ................ 604/95.01 |
| 2001/0053879 A1 | 12/2001 | Mills et al. |
| 2002/0042620 A1 | 4/2002 | Julian et al. |
| 2002/0072704 A1 | 6/2002 | Mansouri-Ruiz |
| 2002/0087169 A1 | 7/2002 | Brock et al. |
| 2002/0120254 A1 | 8/2002 | Julian et al. |
| 2002/0177789 A1 * | 11/2002 | Ferry et al. ................ 600/585 |
| 2002/0183723 A1 | 12/2002 | Belef et al. |
| 2003/0176770 A1 * | 9/2003 | Merril et al. ................ 600/118 |
| 2003/0195605 A1 * | 10/2003 | Kovalcheck et al. ........ 607/138 |
| 2004/0039338 A1 * | 2/2004 | Lee et al. ................ 604/164.12 |
| 2004/0077942 A1 | 4/2004 | Hall et al. |
| 2004/0102740 A1 * | 5/2004 | Meloul .......................... 604/263 |
| 2004/0254566 A1 | 12/2004 | Plicchi et al. |
| 2005/0038412 A1 * | 2/2005 | Rabiner et al. ................ 604/528 |
| 2005/0065435 A1 | 3/2005 | Rauch et al. |
| 2005/0113719 A1 | 5/2005 | Saadat |
| 2005/0125002 A1 * | 6/2005 | Baran et al. ................ 606/108 |
| 2005/0203382 A1 | 9/2005 | Govari et al. |
| 2005/0222554 A1 | 10/2005 | Wallace et al. |
| 2005/0228440 A1 | 10/2005 | Brock et al. |
| 2005/0277874 A1 | 12/2005 | Selkee |
| 2005/0283140 A1 | 12/2005 | Jensen et al. |
| 2006/0009735 A1 | 1/2006 | Viswanathan et al. |
| 2006/0041181 A1 | 2/2006 | Viswanathan et al. |
| 2006/0069311 A1 * | 3/2006 | Sullivan et al. ................ 600/149 |
| 2006/0084911 A1 | 4/2006 | Belef et al. |
| 2006/0084945 A1 | 4/2006 | Moll et al. |
| 2006/0095022 A1 | 5/2006 | Moll et al. |
| 2006/0161136 A1 | 7/2006 | Anderson et al. |
| 2006/0161137 A1 | 7/2006 | Orban et al. |
| 2006/0161138 A1 | 7/2006 | Orban et al. |
| 2006/0167441 A1 | 7/2006 | Wang et al. |
| 2006/0229587 A1 | 10/2006 | Beyar |
| 2006/0235436 A1 | 10/2006 | Anderson et al. |
| 2006/0270915 A1 | 11/2006 | Ritter et al. |
| 2006/0293643 A1 | 12/2006 | Wallace et al. |
| 2007/0012135 A1 | 1/2007 | Tierney et al. |
| 2007/0019330 A1 | 1/2007 | Wolfersberger |
| 2007/0021776 A1 | 1/2007 | Jensen et al. |
| 2007/0043338 A1 | 2/2007 | Moll et al. |
| 2007/0043455 A1 | 2/2007 | Viswanathan et al. |
| 2007/0149946 A1 | 6/2007 | Viswanathan et al. |
| 2007/0233044 A1 | 10/2007 | Wallace et al. |
| 2007/0239172 A1 | 10/2007 | Lee et al. |
| 2007/0250073 A1 | 10/2007 | Brock et al. |
| 2007/0250074 A1 | 10/2007 | Brock et al. |
| 2007/0260115 A1 | 11/2007 | Brock et al. |
| 2007/0276423 A1 | 11/2007 | Green |
| 2007/0283263 A1 | 12/2007 | Zawde et al. |
| 2007/0299479 A1 | 12/2007 | Saksena |
| 2008/0009791 A1 | 1/2008 | Cohen et al. |
| 2008/0039869 A1 | 2/2008 | Mills et al. |
| 2008/0045892 A1 | 2/2008 | Ferry et al. |
| 2008/0059598 A1 | 3/2008 | Garibaldi et al. |
| 2008/0119824 A1 | 5/2008 | Weitzner et al. |
| 2008/0119872 A1 | 5/2008 | Brock et al. |
| 2008/0125793 A1 | 5/2008 | Brock et al. |
| 2008/0125794 A1 | 5/2008 | Brock et al. |
| 2008/0140087 A1 | 6/2008 | Barbagli |
| 2008/0147091 A1 | 6/2008 | Cooper |
| 2008/0215065 A1 | 9/2008 | Wang et al. |
| 2008/0245946 A1 | 10/2008 | Yu |
| 2008/0249536 A1 | 10/2008 | Stahler et al. |
| 2008/0300592 A1 | 12/2008 | Weitzner et al. |
| 2009/0012533 A1 | 1/2009 | Barbagli et al. |
| 2009/0082722 A1 | 3/2009 | Munger et al. |
| 2009/0105639 A1 | 4/2009 | Weitzner et al. |
| 2009/0105645 A1 | 4/2009 | Kidd et al. |
| 2009/0248043 A1 | 10/2009 | Tierney et al. |
| 2011/0166513 A1 | 7/2011 | Cohen et al. |
| 2012/0220931 A1 | 8/2012 | Cohen et al. |

OTHER PUBLICATIONS

Hein et al., "Robot Supported Insertion of Catheters for Hyperthermia and Branch Therapy," Computer Assisted Radiology and Surgery, 1998, pp. 660-663.

Macoviak, "Catheter System for Surgical Access and Circulatory Support of the Heart," USPTO, Official Gazette, vol. 1278, Jan. 6, 2004.

State Intellectual Property Office of the People's Republic of China, First Office Action, Oct. 30, 2009, Chinese Patent Application 200680025512.7, "Remotely Controlled Catheter Insertion System," with English translation, (22 pgs. total).

Chinese Application 200680025512.7, State Intellectual Property Office of the People's Republic of China, Office Action dated Feb. 13, 2012.

Chinese Application 200980102420.8, State Intellectual Property Office of the People's Republic of China, Office Action dated Feb. 16, 2012.

International Preliminary Report on Patentability, Intl Application PCT/US2009/031357. International Bureau of WIPO, Jul. 29, 2010.

International Search Report and Written Opinion, Intl Application PCT/US2009/031357. International Search Authority, U.S. Patent and Trademark Office (ISA/US), Mar. 19, 2009.

U.S. Appl. No. 13/051,736, Final Office Action dated Nov. 5, 2012.

Canadian Application 2,646,846, Office Action dated Sep. 19, 2012.

U.S. Appl. No. 12/903,397, Non-Final Office Action dated Nov. 19, 2012.

U.S. Appl. No. 13/051,736, Non-Final Office Action dated Jul. 17, 2012.

Supplementary European Search Report and Search Opinion for Application No. EP 06 78 6995 from the European Patent Office dated Mar. 25, 2013.

* cited by examiner

REMOTELY CONTROLLED CATHETER INSERTION SYSTEM

CROSS-REFERENCE TO RELATED APPLICATIONS

This application is a divisional application of and claims priority to U.S. patent application Ser. No. 11/485,595 filed Jul. 11, 2006, entitled "Remotely Controlled Catheter Insertion System," which claimed the benefit of priority to U.S. Provisional Patent Application Ser. No. 60/698,271, filed Jul. 11, 2005, entitled "System and Method for Remote Robotic Electrophysiology," each of which is hereby incorporated herein by reference in their entirety.

FIELD OF THE INVENTION

The present invention is directed to the positioning of medical devices within the body of a patient. More particularly, the invention is directed to the positioning of medical devices such as catheters within a patient's body using a remotely controlled system. Alternatively, the invention can also be used to position and deploy pacemaker and/or defibrillator leads.

BACKGROUND

Invasive procedures, such as invasive electrophysiology procedures, are very complicated and presently require the use of radiation, e.g., fluoroscopy, to visualize the location of a device such as a catheter and to help position the device within a patient's body at a site, such as the heart or the circulatory system. To facilitate catheter placement, certain fields, including the field of electrophysiology, have developed multi-poled and shaped steerable catheters. In addition, three-dimensional non-fluoroscopic mapping systems have also been developed to help identify catheter locations in space and to document their locations along with the electrical activity of the heart.

Even with the advent of such catheters and mapping systems, these procedures still can expose the patient, operator, and other staff to high cumulative dosages of radiation which may have long term adverse effects on those exposed. A patient may be directly exposed only once or twice to such procedures; however, a high volume operator and staff can be exposed both directly and indirectly to the radiation during many procedures over a long period of time. To protect the operator and staff from this radiation, shielding comprising lead aprons, gowns, glasses, skirts, etc., is worn. Such lead clothing, especially a lead apron, is quite heavy and uncomfortable, and its use has been associated with cervical and lumbar spine injury.

An alternative to this lead shielding is "imitation" lead, i.e., lead-like substances used as barriers. Even this lighter weight shielding still applies continuous force to the spinal column which can result in discomfort and neck, back, and/or sacral spine injury over time.

In view of the concerns regarding radiation exposure and the drawbacks of lead protection, techniques and systems have been developed so that a physician or technician may be able to control the insertion and movement of a catheter remotely. Commercially available catheters, such as balloon dilatation angioplasty catheters, typically have at least six ranges of motion. Known systems for remote control of catheters require the use of specialized catheters compatible with a particular system, which catheters are more expensive than the commercially available, "off the shelf" catheters. Also, the known remote controlled catheter insertion systems have controls that are not intuitive and do not conform to procedures generally taught in medical school. As consequence, a user is required to learn a new device and new movement controls for insertion of the catheter.

Thus, there is a need for a remotely controllable catheter insertion system which can utilize commercially available catheters and take advantage of the known features of such catheters. This will enable the user to utilize the device using a control input which is comfortable and familiar to the user.

OBJECTS OF THE INVENTION

It is an object of the invention to provide an apparatus and method for positioning a medical device within a patient.

It is a also an object of the invention to provide an apparatus and method for positioning a medical device such as a catheter within a patient's body using a remotely controlled robotic system.

It is a further object of the invention of the invention to provide a system for remotely controlling the positioning within the body of a patient of a medical device having a control handle, the system comprising:

a robotic device configured to position the medical device within the body of the patient; and a remote control mechanism configured to control the robotic device, wherein the robotic device comprises a modular handle controller to receive the control handle.

It is a further object of the invention to provide a method of inserting elongated medical devices into a patient using such a system and performing any one of a number of diagnostic and/or therapeutic procedures.

These and other objects of the invention will be more apparent in the description below.

SUMMARY OF THE INVENTION

According to the invention, a system and method are provided for remotely controlling a robotic device to insert and position a medical device such as a catheter within the body of a human or animal patient. The device can be visualized by use of standard fluoroscopy (with X rays), cine angiography, and/or three-dimensional mapping non-fluoroscopic imaging modalities, which can have direct and/or remote monitoring capabilities or otherwise. Certain embodiments of the invention allow an operator, such as a doctor or other medical professional, to be positioned at a location that is remote from the actual location of a patient, and to use a remote control mechanism comprising a remote control station and a controller to control a robotic device to insert, place, and position medical devices such as catheters within the body of the patient. The catheter may be fed into a nonvascular part of the body in order to find a target and record, diagnose, and/or deliver treatment or therapy. The catheter feeder may be driven by a telescoping rod without rotors. A system may integrate an imaging modality with a remote monitor and the medical device may be positioned in the body by remotely visualizing the medical device. The device may then be positioned using a system as discussed above.

In one embodiment of the invention, venous or arterial vascular access or nonvascular access is performed directly by an operator, and a medical device such as a catheter is inserted into an introducer sheath and then fed and advanced and steered to the appropriate location. In another embodiment of the invention, vascular access can also be obtained. In such embodiments, the operator of the medical procedure can advance, remove, shape, steer, and deflect a standard electrophysiology catheter, such as an ablation catheter, within the patient from a location remote from the patient, such as a shielded control room, and avoid exposure to potentially harmful radiation normally associated with such a procedure. In this manner, the present invention may eliminate the need for doctors or other medical personnel, to wear protective gear in performing such medical procedures, which may be uncomfortable, less than fully effective, and cause injury to the wearer over time.

In another embodiment of the invention, a system and method control a robotic device to position a medical device, such as a catheter, within the body of a patient. The medical device is an elongated medical device having a control handle, examples of which include catheters, guidewires, introducer sheaths or catheters, and guide sheaths or catheters. Examples of specific catheters include, but are not limited to, ablation catheters, mapping catheters, balloon dilatation catheters, perfusion catheters, pacing and/or defibrillation leads, and the like. This embodiment may comprise a robotic device configured to position the medical device within the body of the patient and a remote control mechanism or system configured to control the robotic device to position the medical device. The remote control mechanism preferably comprises (1) a remote control station and (2) a controller in communication with the remote control station. The robotic device preferably has a handle controller to receive the control handle of the medical device. The remote control mechanism may comprise a remote control station and a robotic device controller wherein an operator, such as a doctor or other medical professional, uses the remote control station to control the robotic device. The remote control station will comprise appropriate control knobs, levers, switches, buttons, slides, or other controls, such as a joystick.

When manipulated by hand, modem catheter devices are capable of moving in up to six ranges of motion. For example, catheters can clearly be moved forward and backward so that a longer portion of the catheter may be inserted into a subject and removed. Catheters may also be rotated clockwise and counterclockwise. Moreover, the distal end or tip of many catheters, referred to as "steerable", can be deflected in several directions.

The remote control mechanism may also include one or more transmitters, receivers, or transceivers to communicate information between the remote control station and the robotic device controller, by any wired and/or wireless transmission mechanism, including via dial-up, cable, or broadband modem internet transmission. The operator may control the robotic device from a location that is remote from the location of the patient, including, but not limited to, a shielded control room. The robotic device may include one or more sensors to communicate information to the remote control station regarding movement of the catheter and the environment of the catheter within the patient's body.

In another embodiment of the invention, the robotic device may be configured to allow the operator to insert the medical device within the body of the patient and position the medical device within the body of the patient. The medical device may be a catheter, and the robotic device may be a catheter control device configured to allow the operator, using the remote control device, to do one or more of the following within the patient's body: insert the catheter, advance or feed the catheter, steer the catheter, rotate the catheter, place the catheter, shape the catheter, or deflect the catheter. The catheter or other medical device may be inserted into and positioned within a variety of portions and systems of the patient's body, such as within the heart or the circulatory system of the patient.

In another embodiment of the invention, the elongated medical device may be a catheter, such as an electrophysiology catheter and/or an interventional catheter. The catheter or other medical device may be used for a cardiac, vascular, radiological, gastroenterological, or nephrological procedure or for a combination of two or more such procedures, and it may optionally be used to deliver therapy for such procedures, including the delivery of biologicals such as stem cells, angiogenesis factors, etc. The catheter may also be used for mapping, catheter ablation, stenting, angioplasty, atrial fibrillation ablation, ventricular tachycardia ablation, and/or other complex forms of catheter ablation (e.g., multiple atrial tachycardias, etc.), or delivery of drugs or medicine, or a combination of two or more of such procedures.

In another embodiment of the invention, a robotic device comprises a catheter feeder and a handle control assembly. In a further embodiment of the invention, the control device may include a catheter feeder, a clamp model, a handle control assembly, and/or a catheter control assembly. The feeder system may include an outer housing assembly, wherein the outer housing assembly may include an outer ring and one or more gears, and a clamp assembly, wherein the clamp assembly may include one or more clamp brackets, clamps, or belts. The device may be designed so as to avoid hard wiring in the outer ring. For example, contacts may be used to electrify the motor and deflect the tip. The handle assembly may include a handle outer housing assembly comprised of an outer ring and one or more gears. The control device may further include a means for holding said medical device firmly, a means for rotating said medical device, and a means for one or more of the following: shaping, deflecting, steering, placing, or positioning the medical device within the patient.

In another embodiment of the invention, the remote control station may comprise a joystick. In a further embodiment of the invention, a computer guided navigation system may be employed with a similar or equivalent catheter introducer system with sensor feedback to translate the actual resistance to movement, tip pressure and catheter motion which is occurring in the body to the remote catheter introducer system/model. A human model with traditional sheath and catheter appearance, with sensors, can serve as the controller translating information to the handle control device and feeder system. This set up could allow the operator to insert and manipulate a catheter by standard fashion, remotely and transmit and manipulate an interventional catheter within the human body.

The remote control mechanism may optionally include an apparatus or model in which a catheter is introduced or manipulated, similar to that which is inserted into the human body. That catheter and model control mechanism can transmit information back and forth to the catheter handle control device and catheter feeder system so as to translate manipulation, performed remotely to the actual invasive system. Sensors and registers exist in the model (remote control mechanism) to convey the actual feel of the invasive catheter to that of the catheter model remote controller. In one embodiment, the apparatus or model resembles the human anatomy for catheter insertion. Such a model can comprise an introducer sheath; a catheter and handle and gears; and sensors, resistors, and transistors. In another embodiment of the invention, when integrated with imaging modalities such as 3D mapping, the remote control is a computer in which catheter translations, movement/manipulations, can be remotely performed (possibly automatically with the ability for human intervention and/or input) by safe iterative steps in order to safely reach targeted sites for catheter deployment.

In another embodiment of the invention, handles, knobs, and/or switches on a catheter handle are manipulated as the remote control is translated into precise movement and feel of a similar catheter which is inserted and manipulated robotically within the human body.

In a further embodiment of the invention, a robotic device comprises:

a handle controller effective to receive the control handle of a medical device, the medical device having at least three ranges of motion and a distal end;

a first motor in communication with the handle controller and capable of moving the medical device in the axial direction;

a second motor in communication with the handle controller and capable of rotating the distal end of the medical device;

a third motor in communication with the handle controller and capable of deflecting the distal end of the medical device; and a control unit in communication with the first, second, and third motors.

In a further embodiment of the invention, the first motor is connected to an externally threaded drive screw, the handle controller is connected to an internally threaded drive support, and the drive screw is mated with the drive support. The handle controller is connected to a telescoping rod so that when the catheter is inserted into the handle controller, a sheath of the catheter is inserted into the telescoping rod, and the telescoping rod is connected to a catheter feeder. The catheter feeder may comprise a clip or attachment at the distal end of the catheter feeder that attaches to the proximal outer housing of a standard introducer sheath to deliver the catheter into the patient's body without buckling.

In other embodiments of the invention, there can be more or less than three motors. In addition, there can be a backend unit to control a second medical device such as, for example, a catheter, stylette, or guidewire. For example, the first component system may control a steerable sheath, and a second, backend system or controller may control a steerable catheter. Thus, there can be a plurality of controllers to achieve additional maneuverability.

In a further embodiment of the invention, a sensor is disposed proximate to the first motor, the sensor effective to detect movement of the first motor.

In a further embodiment of the invention, the handle controller further includes a stabilizer bar effective to receive a flexible portion of the catheter.

In a further embodiment of the invention, the stabilizer bar is effective to mate with the flexible portion of the catheter in a snap-fit manner. A force sensor can be configured into the stabilizer bar to record pressure upon moving the catheter forward. This is especially useful if the inner housing is floating such that all translation force is conveyed to that stabilizer bar.

In a further embodiment of the invention, the handle controller is detachably mounted to a rotation assembly.

In a further embodiment of the invention, the handle controller includes a cylinder, and the second motor is connected to a drive wheel connected to the cylinder.

In a further embodiment of the invention, the rotation assembly includes the drive wheel and a driven wheel.

In a further embodiment of the invention, the rotation assembly further includes a support wheel.

In a further embodiment of the invention, the support wheel is grooved.

In a further embodiment of the invention, the handle controller further includes a slip ring.

In a further embodiment of the invention, a sensor is disposed proximate to the second motor, the sensor effective to detect a movement of the second motor.

In a further embodiment of the invention, the catheter includes a knob effective to control deflection of the distal end; and the third motor is connected to the knob.

In a further embodiment of the invention, the third motor is connected to the knob through at least one gear.

In a further embodiment of the invention, the third motor is connected to the knob through a first, second and third gear, the third gear including a gear extension defining an opening for placement of the knob.

In a further embodiment of the invention, a sensor is disposed proximate to the third motor, the sensor effective to detect a movement of the third motor.

In a further embodiment of the invention, the catheter includes a knob effective to control deflection of the distal end; and the third motor is connected to the knob.

In a further embodiment of the invention, the third motor is connected to the knob through at least one gear.

In a further embodiment of the invention, the third motor is connected to the knob through a first, second and third gear, the third gear including a gear extension defining an opening for the knob.

In a further embodiment of the invention, the control unit is connected to the first, second and third motor through the use of wires.

In a further embodiment of the invention, the control unit is connected to the first, second and third motor wirelessly.

In a further embodiment of the invention, the control unit includes a separate control for each of the first, second and third motors.

In a further embodiment of the invention, a method for using a remotely controlled catheter movement device, comprises:

inserting a first catheter into a first handle;
inserting the first handle into the device;
operating the device;
removing the first catheter and the first handle;
inserting a second catheter into a second handle, the second catheter having a distinct structure from the first catheter;
inserting the second handle into the device;
operating the device.

In a further embodiment of a method of the invention, the handles are inserted into a rotation assembly.

In a further embodiment of the invention, the rotation assembly includes a driving wheel, a driven wheel and a support wheel.

In a further embodiment of the invention, the inserting the first catheter into the first handle includes inserting the first catheter into a stabilizer bar.

In a further embodiment of the invention, the inserting the first catheter into the first handle includes connecting the first catheter to a motor, the motor effective to impart deflection to a tip of the first catheter.

In a further embodiment of the invention, the inserting the first catheter into the first handle includes clamping the first catheter to the first handle.

In a further embodiment of the invention, in a system for remotely controlling the positioning of a medical device within the body of a patient, the system comprises a robotic device configured to position the medical device within a body of a patient. The robotic device comprises a handle controller effective to manipulate any control on the medical device, a driver effective to move the medical device forward and backward, and a catheter feeder effective to deliver the medical device inside the body. The device further includes a remote control mechanism effective to control the robotic device.

The medical device could be a catheter, guidewire, introducer sheath, or guide catheter or a pacemaker or defibrillator lead. The handle controller may be modular with each module adaptable to a certain type of catheter or other medical device. The handle controller may be configured to the shape of a specific catheter. The handle controller may be configured to control features of the catheter in order to change its shape, contour, and to deflect the catheter. The catheter feeder could include a telescoping unit. The telescoping unit could be sterile or disposable. The catheter could be a lead that senses, paces, and or performs defibrillation. The catheter could be placed at locations including the right atrium, the right ventricle, the left atrium, the left ventricle, the endocardium of the heart, the epicardium of the heart, etc.

In a further embodiment of the invention, the remote control mechanism comprises a remote control station and a robotic device controller, an operator using the remote control station to control the robotic device.

In a further embodiment of the invention, the remote control mechanism includes one or more transmitters, receivers, and/or transceivers to communicate information between the remote control station and the robotic device controller.

In a further embodiment of the invention, the robotic device is controlled from a remote control station at a location that is remote from the location of the patient, such as a shielded control room.

In a further embodiment of the invention, the handle controller is modular.

In a further embodiment of the invention, the modular handle controller is designed specifically to control a particular type or model of medical device.

In a further embodiment of the invention, the modular handle controller is designed specifically to control a particular catheter handle and its controls.

In a further embodiment of the invention, the modular handle controller is designed specifically to control delivery, positioning, and placement of a pacemaker and/or defibrillator lead.

In a further embodiment of the invention, the handle controller can be adapted to conform to a variety of different medical devices.

In a further embodiment of the invention, the handle controller of the robotic device engages the control handle of the catheter.

In a further embodiment of the invention, the handle controller uses the standard features of the catheter control handle to, within the body of the patient, insert the catheter, steer the catheter, rotate the catheter, place the catheter, shape the catheter, or deflect the catheter, or a combination of two or more thereof.

In a further embodiment of the invention, the catheter is used for mapping and catheter ablation.

In a further embodiment of the invention, the catheter is used for stenting, angioplasty, or drug delivery or a combination of two or more thereof.

In a further embodiment of the invention, the handle controller further includes a catheter feeder system.

In a further embodiment of the invention, the handle controller further comprises a clamp; a handle assembly; and a catheter control assembly.

In a further embodiment of the invention, the handle controller further comprises:

an outer housing assembly, wherein the outer housing assembly includes an outer ring and one or more gears; and a clamp assembly effective to clamp the control handle of the medical device to the handle controller, wherein the clamp assembly includes one or more clampbrackets, clamps, or belts.

In a further embodiment of the invention, handle assembly includes a handle outer housing assembly comprised of an outer ring and one or more gears.

In a further embodiment of the invention, the handle controller further comprises:

means for holding said catheter firmly;

means for rotating said catheter; and means for shaping, deflecting, steering, placing, or positioning the catheter, or a combination of two or more thereof, within the patient.

In a further embodiment of the invention, the handle controller further includes one or more sensors to communicate information to the remote control device regarding movement of the catheter and the environment of the catheter within the patient's body.

In a further embodiment of the invention, the information is communicated to the remote station.

In a further embodiment of the invention, the remote control mechanism comprises information regarding manual introduction or manipulation of a catheter into the human body, and the control mechanism can transmit information back and forth to the catheter handle control device and catheter feeder system so as to translate manipulation, performed remotely to the actual invasive system.

In a further embodiment of the invention, the remote control comprises a computer in which catheter movement and manipulations can be remotely performed by safe iterative steps to safely reach targeted sites for catheter deployment.

In a further embodiment of the invention, the iterative steps are performed with human oversight.

In a further embodiment of the invention, the handles, knobs, switches, or controls on a catheter control handle are manipulated by the handle controller to approximate the precise movement and feel of a similar catheter which is inserted and manipulated manually within the human body.

In a further embodiment of the invention, a system is securely affixed to a base or support so that a medical device can be delivered to a patient in a stable, predictable, and secure manner.

In a further embodiment of the invention, the system is mounted to a ceiling, table, wall, floor, tripod, or cart with locking wheels.

In a further embodiment of the invention, the medical device is a pacemaker and/or defibrillator lead.

In a further embodiment of the invention, the robotic device can advance and remove the lead and/or rotate the lead clockwise and counter-clockwise.

In a further embodiment of the invention, a system also includes means for securing and/or deploying a lead for pacing or shocking, i.e., cardioverting or defibrillation, within the coronary sinus vein or its branches.

In a further embodiment of the invention, a lead capable of applying low and/or high voltage therapy to the left atrium or the left ventricle is deployed.

In a further embodiment of the invention, the medical device is a guidewire or stylette.

In a further embodiment of the invention, the robotic device can advance and remove the guidewire or stylette and/or rotate the guidewire or stylette clockwise and counter-clockwise.

In a further embodiment of the invention, the electrophysiology catheter is a mapping and/or ablation catheter.

In a further embodiment of the invention, a system can be used to perform atrial fibrillation ablation.

In a further embodiment of the invention, a system can be used to perform ventricular tachycardia ablation.

In a further embodiment of the invention, a system can be used to perform atrial flutter ablation.

In a further embodiment of the invention, a system can be used to perform atrial tachycardia ablation.

In a further embodiment of the invention, a system can be used to perform pulmonary vein isolation.

In a further embodiment of the invention, a system can be used to perform simple ablations or complex ablations.

In a further embodiment of the invention, a system can be used to perform complex ablations for accessory pathway mediated tachycardias.

In a further embodiment of the invention, a system has limiters to limit the advancement or withdrawal of a medical device.

In a further embodiment of the invention, the robotic device comprises:

a handle controller effective to receive a control handle of a catheter, the catheter having at least three ranges of motion and a distal end;

a first motor connected to the handle controller and effective to at least move the catheter forward and/or backward;

a second motor connected to the handle controller and effective to at least rotate the catheter;

a third motor connected to the handle controller and effective to at least deflect the distal end in at least a first direction; and a controller unit connected to the first, second and third motors.

In a further embodiment of the invention, the first motor is connected to an externally threaded drive screw; the handle controller is connected to an internally threaded drive support; and the drive screw is mated with the drive support.

In a further embodiment of the invention, the handle controller is connected to a telescoping rod so that when the catheter control handle is inserted into the handle controller, the distal end of the catheter is inserted into and through the telescoping rod.

In a further embodiment of the invention, the telescoping rod extends from the handle controller to the catheter feeder.

In a further embodiment of the invention, the telescoping rod is a collapsible tube with an inner diameter which can easily deliver a medical device such as a catheter or lead without buckling.

In a further embodiment of the invention, the telescoping rod is constructed of interlocking cylinders such that the cylinder closest to the handle controller is larger than the cylinder farthest from the handle controller.

In a further embodiment of the invention, the telescoping rod is sterile.

In a further embodiment of the invention, the telescoping rod is disposable.

In a further embodiment of the invention, the telescoping rod is sterilizable.

In a further embodiment of the invention, the telescoping rod is connected to a catheter feeder, the catheter feeder including a clip effective to inhibit buckling of the sheath.

In a further embodiment of the invention, a specially designed clip can securely attach the end of the controller to an introducer sheath to maintain a short fixed distance and prevent catheter buckling during remote catheter manipulation.

In a further embodiment of the invention, the clip is sterile.

In a further embodiment of the invention, the clip is disposable.

In a further embodiment of the invention, clip is sterilizable.

In a further embodiment of the invention, a system further comprises a sensor disposed proximate to the first motor, the sensor being effective to detect a movement of the first motor.

In a further embodiment of the invention, the handle controller further includes a stabilizer bar effective to receive a flexible portion of the catheter.

In a further embodiment of the invention, the stabilizer bar is effective to mate with the flexible portion in a snap-fit manner.

In a further embodiment of the invention, a system further comprises a sensor disposed proximate to the stabilizer bar, the sensor being effective to detect movement of the catheter.

In a further embodiment of the invention, a system further comprises a limiter connected to the sensor and effective to limit the first motor.

In a further embodiment of the invention, the handle controller is detachably mounted to a rotation assembly.

In a further embodiment of the invention, the handle controller includes a cylinder and the second motor is connected to a drive wheel connected to the cylinder.

In a further embodiment of the invention, the rotation assembly includes the drive wheel and a driven wheel.

In a further embodiment of the invention, the rotation assembly further includes a support wheel.

In a further embodiment of the invention, the support wheel is grooved.

In a further embodiment of the invention, the handle controller further includes a slip ring.

In a further embodiment of the invention, a system further comprises a sensor disposed proximate to the second motor, the sensor being effective to detect a movement of the second motor.

In a further embodiment of the invention, the catheter includes at least one control member effective to control deflection of the distal end and the third motor is connected to the at least one control member.

In a further embodiment of the invention, each control member is a switch, knob, lever, slide, gear, or button.

In a further embodiment of the invention, the third motor is connected to the at least one control member through at least one gear.

In a further embodiment of the invention, the third motor is connected to the at least one control member through a first, second and third gear, the third gear including a gear extension defining an opening for placement of the at least one control member.

In a further embodiment of the invention, a sensor is disposed proximate to the third motor, the sensor being effective to detect a movement of the third motor.

In a further embodiment of the invention, the catheter includes at least one control member effective to control deflection of the distal end and the third motor is connected to the at least one control member.

In a further embodiment of the invention, the third motor is connected to the at least one control member through at least one gear.

In a further embodiment of the invention, the third motor is connected to the at least one control member through a first, second and third gear, the third gear including a gear extension defining an opening for the knob.

In a further embodiment of the invention, the control unit is connected to the first, second and third motor through the use of wires.

In a further embodiment of the invention, the control unit is connected to the first, second and third motor wirelessly.

In a further embodiment of the invention, the control unit includes a separate control for each of the first, second and third motors.

In a further embodiment of the invention, the robotic device is configured so that any tubing or wires extending into the medical device do not get tangled as the medical device is rotated.

In a further embodiment of the invention, there is a rotating connector in communication with the proximal end of the medical device.

In a further embodiment of the invention, the medical device is a commercially available steerable catheter, introducer sheath, pacing or defibrillation lead, guidewire, or stylette.

In a further embodiment of the invention, a method for using a remotely controlled robotic catheter device, the method comprises:
  inserting the control handle of a first catheter into a first handle controller;
  inserting the first handle controller into the robotic device;
  operating the device;
  removing the first catheter and the first handle controller;
  inserting the control handle of a second catheter into a second handle controller, the second catheter having a structure distinct from the structure of the first catheter;
  inserting the second handle controller into the robotic device; and
  operating the device.

In a further embodiment of the invention, the handle controllers are inserted into a rotation assembly.

In a further embodiment of the invention, the rotation assembly includes a driving wheel, a driven wheel and a support wheel.

In a further embodiment of the invention, inserting the control handle of the first catheter into the first handle controller includes inserting the first control handle into a stabilizer bar.

In a further embodiment of the invention, the inserting the first catheter control handle into the first handle controller includes connecting the first catheter to a motor, the motor effective to impart deflection to a distal tip of the first catheter.

In a further embodiment of the invention, inserting the first catheter control handle into the first handle controller includes clamping the first catheter control handle to the first handle controller.

In a further embodiment of the invention, the medical device is a commercially available steerable catheter, introducer sheath, pacing and/or defibrillation lead, guidewire, or stylette.

In a further embodiment of the invention, in an improved method of mapping, tracking, or delivering therapy with a medical device in combination with an imaging technique, the improvement comprises using a remote positioning control system of the invention to position the medical device.

In a further embodiment of the invention, in an improved method for mapping and catheter ablation by inserting a mapping and ablation catheter into a patient, the improvement comprises using a remote positioning control system of the invention to position the catheter.

In a further embodiment of the invention, a pacing and/or defibrillation lead is placed, deployed, and/or screwed in.

In a further embodiment of the invention, a pacing and/or defibrillation lead is remotely delivered to the right atrium, left atrium, right ventricle, or left ventricle.

In a further embodiment of the invention, a lead is delivered epicardially, endocardially, or via the coronary sinus vein.

In a further embodiment of the invention, a system for remotely controlling the positioning of a medical device within the body of a patient, the system comprises:
  a robotic device configured to position the medical device within a body of a patient;
  the robotic device comprising:
    a handle controller effective to manipulate any control on the medical device;
    a driver effective to move the medical device forward and backward; and
    a catheter feeder effective to deliver the medical device inside the body; and
  a remote control mechanism effective to control the robotic device.

In a further embodiment of the invention, a system wherein the handle controller is modular, each module is adaptable to a particular type of medical device.

In a further embodiment of the invention, the handle controller is adaptable to a variety of medical devices.

In a further embodiment of the invention, a system for remotely controlling the positioning within the body of a patient of an elongated medical device having a proximal end, the system comprises:
  a robotic device configured to position the medical device within the body of the patient; and
  a remote control mechanism configured to control the robotic device,
  wherein the robotic device comprises a handle controller to receive the proximal end of the medical device.

In a further embodiment of the invention, a system for remotely controlling the positioning of a medical device within the body of a patient, the system comprises:
  a robotic device configured to position the medical device within a body of a patient; the robotic device comprising:
    at least two controllers; a distal controller to control a larger medical device, and a proximal controller to control a smaller medical device which is sent through the larger one; wherein the controllers are effective to manipulate any controls on the medical devices and or the medical devices themselves;
    at least two drivers effective to move the proximal medical device forward or backwards within a distal medical device, with the ability to advance the distal medical device forward independent of the proximal medical device;
    a catheter feeder effective to deliver the medical devices inside the body; and
    a remote control mechanism effective to control the robotic device.

In a further embodiment of the invention, telescoping rod is constructed of interlocking cylinders such that as the cylinders get closer to the handle controller they get progressively smaller.

In a further embodiment of the invention, telescoping rod is constructed of interlocking cylinders such that as the cylinders get closer to the handle controller they get progressively larger.

BRIEF DESCRIPTION OF THE DRAWINGS

The following drawing figures, which are included herewith and form a part of this application, are intended to be illustrative and not limiting of the scope of the present invention.

DETAILED DESCRIPTION OF THE INVENTION

Figure 1:
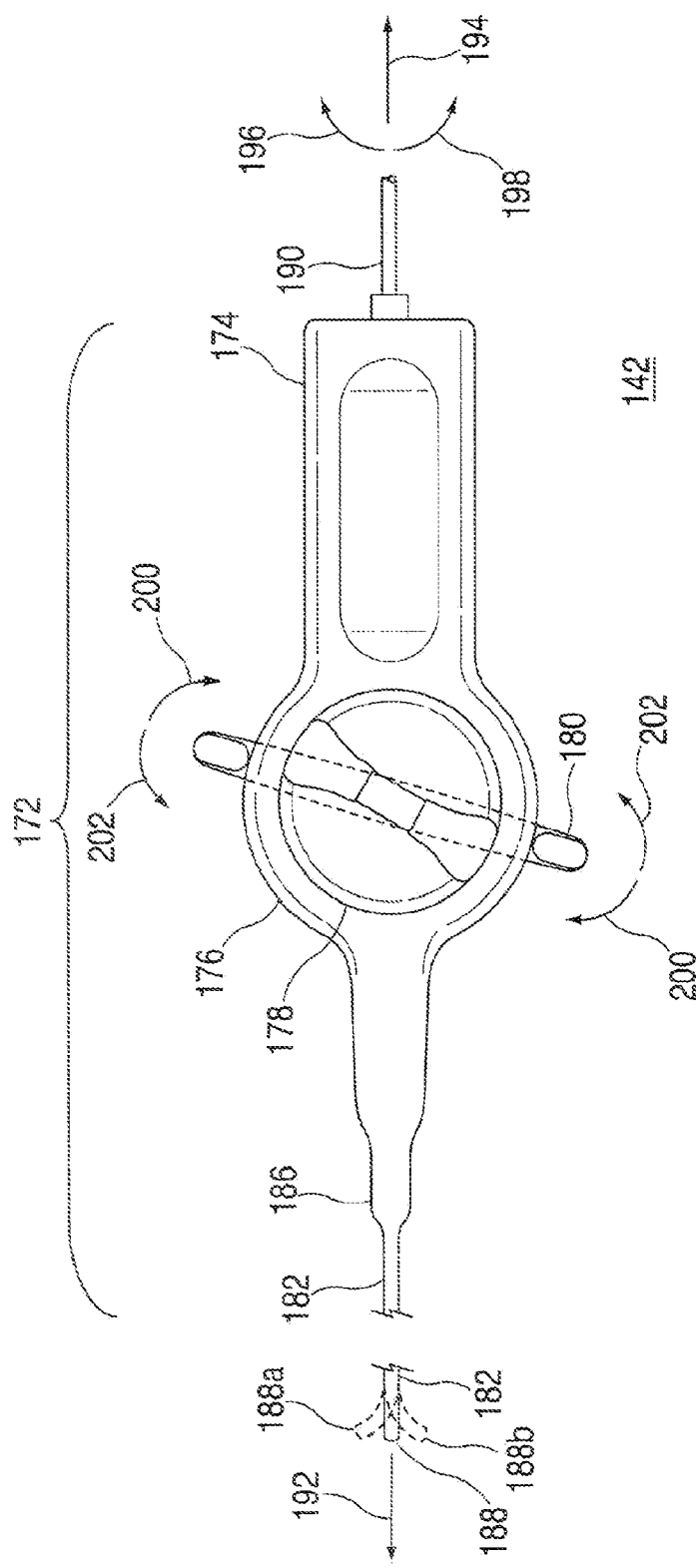
FIG. 1 is a top view of a catheter which could be used in accordance with an embodiment of the invention.

The invention can perhaps be better appreciated by making reference to the drawings. In FIG. 1, a catheter 142 is shown in schematic fashion, which catheter could be used in accordance with an embodiment of the invention. Catheter 142 comprises a handle portion 172 which may be gripped by a user. Handle portion 172 comprises a proximal end 174 and a grip portion 176. Inserted into proximal end 174 may be wires 190 or tubing which could provide electricity, coolant, heat, etc., to catheter 142. Grip 176 comprises an adjustment dial 178 which may be used to adjust the tension of a knob 180. Handle 172 terminates in a distal flexible end portion 186 which in turn is in communication with a distally extending catheter sheath or tubular member 182.

As it is known in the art, catheter sheath 182 may be inserted into a patient by use of various known procedures and devices. Catheter sheath 182 terminates in a distal end 188. Distal end 188 may include, for example, electrodes for supplying electrical stimulation, coolant, heat, etc.

Catheter sheath 182 is physically attached to handle 172 so that movement of handle 172 forward or backward in direction arrow 192 or 194 causes catheter sheath 182, as well as distal end 188, to move similarly. Rotation or torquing of handle 172 in a clockwise or counterclockwise manner as is shown by arrows 196 and 198, will impart a similar rotation to catheter sheath 182. Rotation of knob 180 in the direction or arrow 200 or 202 causes deflection of distal end 188 in one of directions such as are shown at 188a and 188b. Thus, when used manually, commercially available catheters can operate in six ranges of motion: forward and backward in the direction of arrows 192 and 194, rotatable in the direction arrows 196 and 198, and deflectable to positions such as at 188a and 188b. Known remote control catheter insertion devices are not capable of utilizing all of these ranges as a device in accordance with the invention can.

The embodiment shown in the drawings primarily relates to the application of the invention to a steerable catheter. However, the robotic control system of the invention is also applicable to other flexible medical devices such as guidewires, introducer sheaths, guiding catheters, or any similar medical device.

Figure 2:
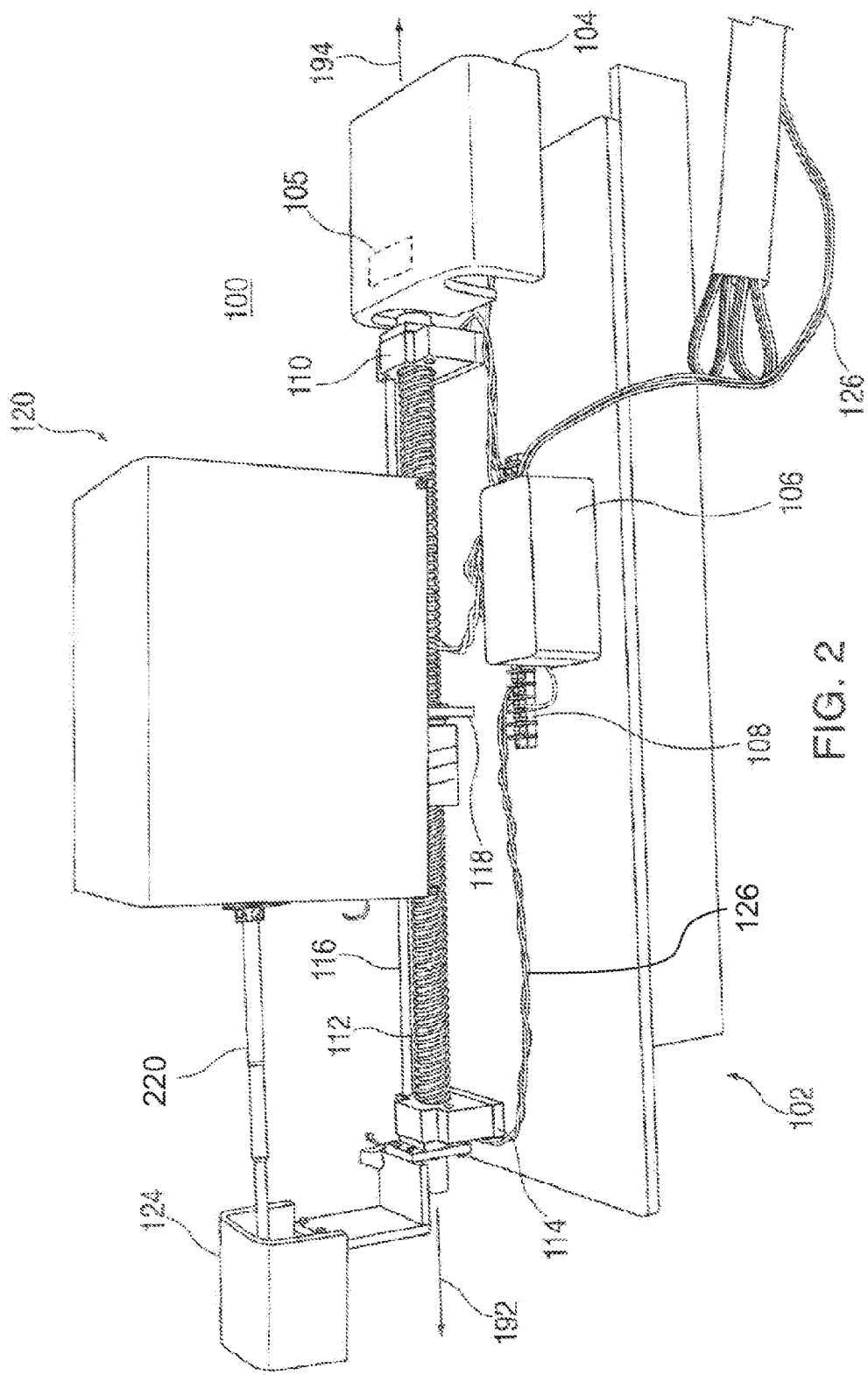
FIG. 2 is a front view of the remotely controlled catheter insertion system in accordance with an embodiment of the invention.
Figure 3:
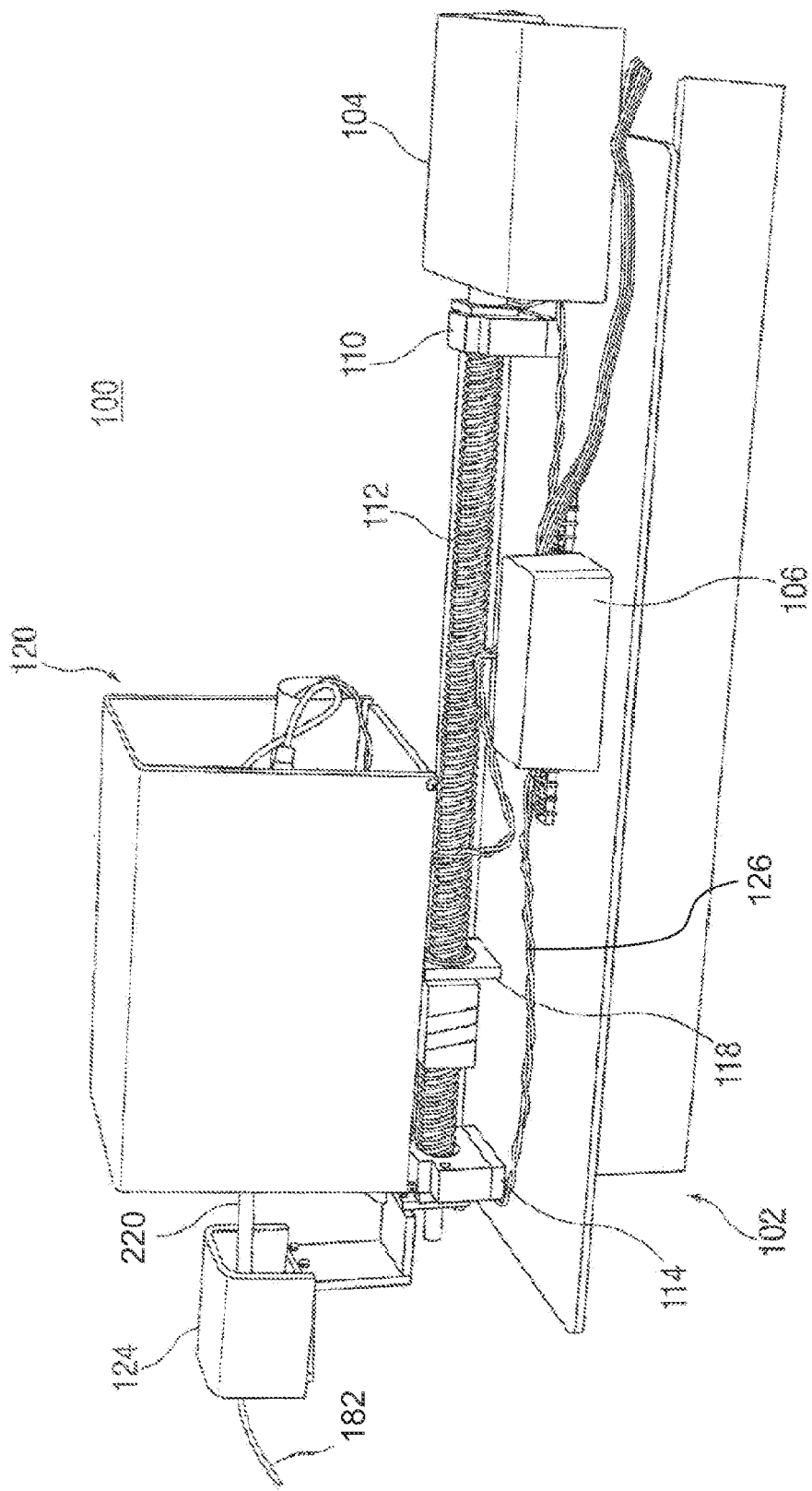
FIG. 3 is a front view of a remotely controlled catheter insertion system in accordance with an embodiment of the invention.

With regard to FIGS. 2 and 3, there is shown a remotely controlled catheter insertion system 100 which could be used in accordance with the embodiment of the invention. System 100 includes a base 102 which supports a motor housing 104, a handle controller 120, a telescoping catheter support tube 122, and a catheter feeder 124. Motor housing 104 houses a motor 105 which receives power and signal control through the use of wires 126 fed through a wire housing 106 and terminal connectors 108. Wires 126 are also fed to handle controller 120 via terminal connectors 108. As discussed in more detail below, wires 126 supply both power and signal control to motor 105 and handle controller 120.

Handle controller 120 is movably supported on base 102 through a metal drive screw 112. Handle controller 120 is connected to drive screw 112 through a drive support 118. Drive support 118 is internally threaded and the internal threads of drive support 118 mate with the external threads of drive screw 112. In this way, when drive screw 112 rotates, drive support 118 to moves laterally (in the figures from left to right and right to left or in directions 192 and 194) due to the engagement of internal threads in drive support 118 and the external threads of drive screw 112. Stoppers 110 and 114 limit the movement of drive support 118 and thereby, in turn, limit the movement of handle controller 120.

Figure 4:
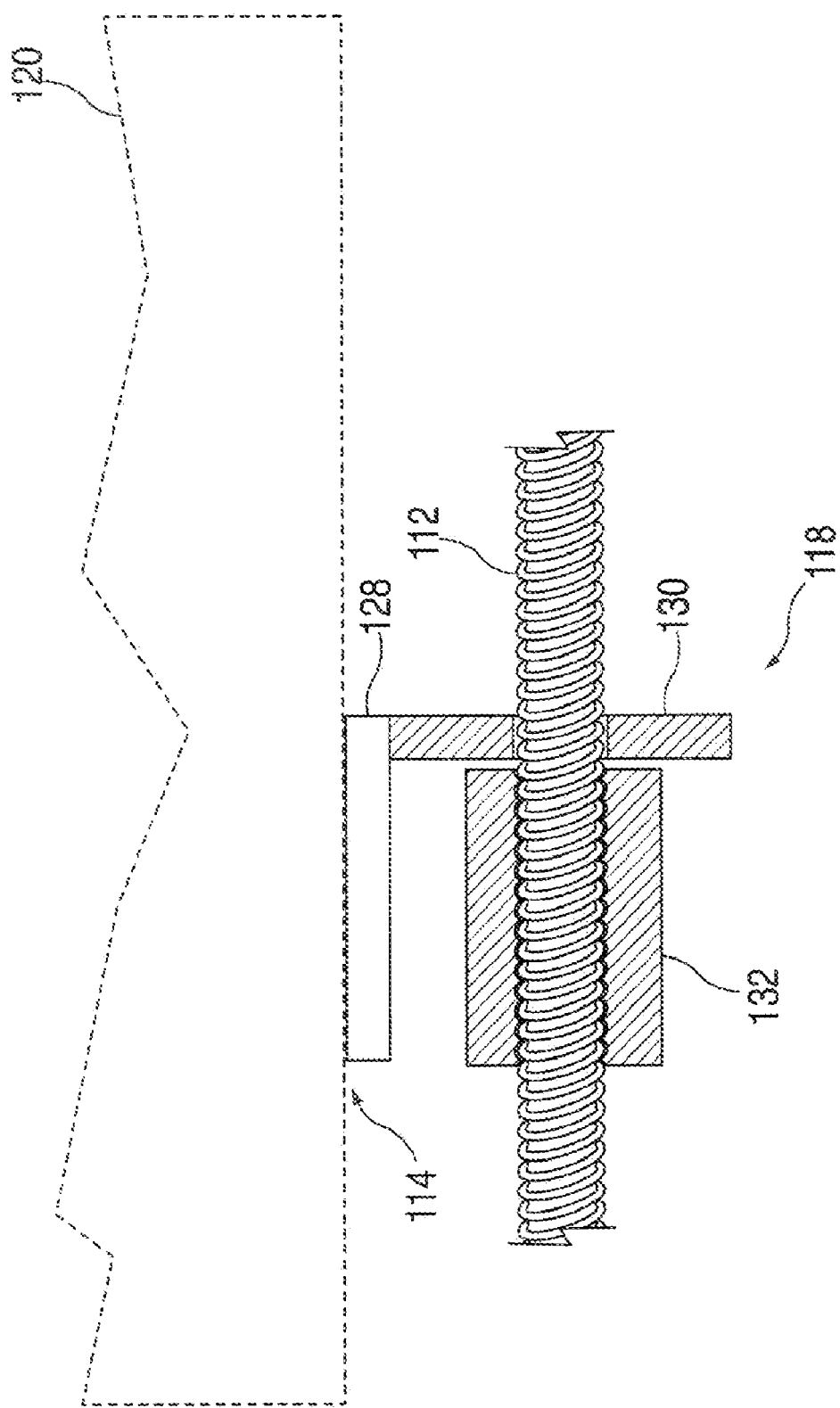
FIG. 4 is a lateral cutaway view of a drive support in accordance with an embodiment of the invention.

As shown most clearly in FIG. 4, drive support 118 includes a support base 130 attached to a cantilevered top support 128 and attached to an internally threaded member 132. Top support 128 is attached to a support base 114 of handle controller 120. As shown in dotted lines, drive screw 112 is fed through a hole in support base 130 and mates with threads of internally threaded member 132. Returning to FIGS. 2-4, in this way, rotation of drive screw 112, causes internally threaded member 132 to move backward or forward (i.e., left or right, direction 192 or 194). Such movement is imparted to support base 130, to top support 128, and then, in turn, to handle controller 120. A sensor may be disposed proximate to motor 105, drive screw 112, drive support 118 or handle controller 120 to sense a movement of handle controller 120.

Figure 5:
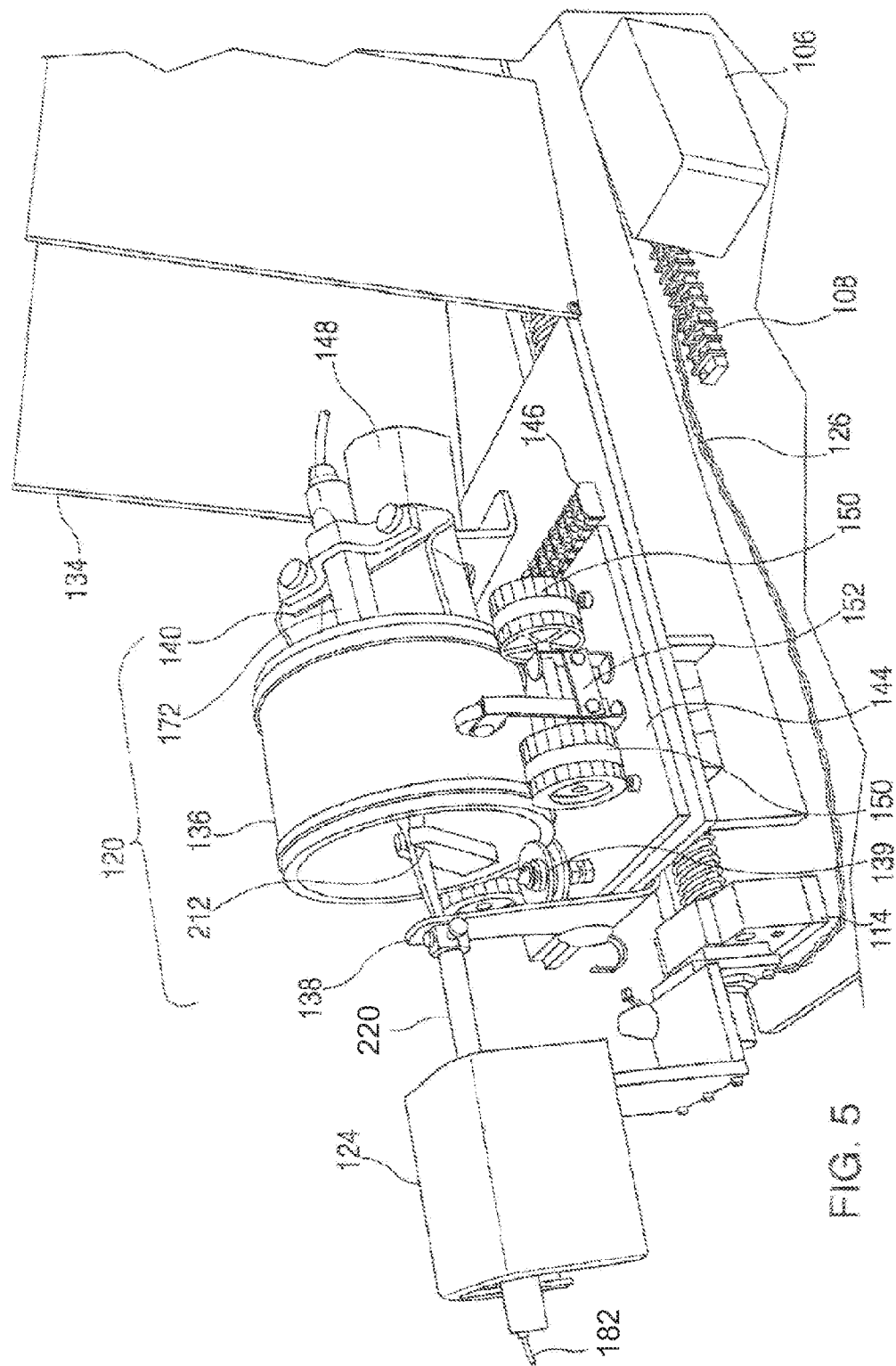
FIG. 5 is a perspective view of a handle controller in accordance with an embodiment of the invention.
Figure 6:
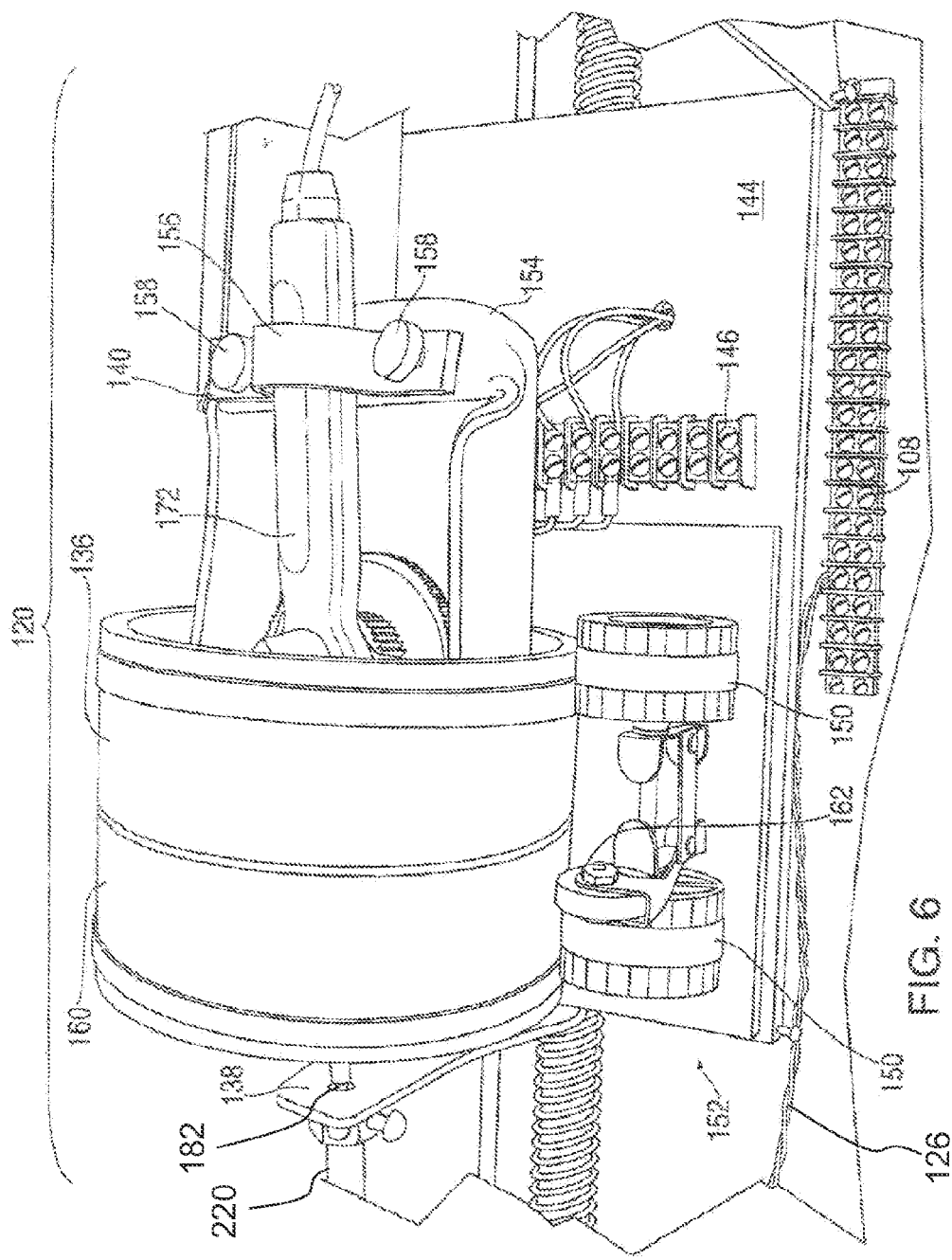
FIG. 6 is a perspective top view of a handle controller in accordance with an embodiment of the invention.
Figure 7:
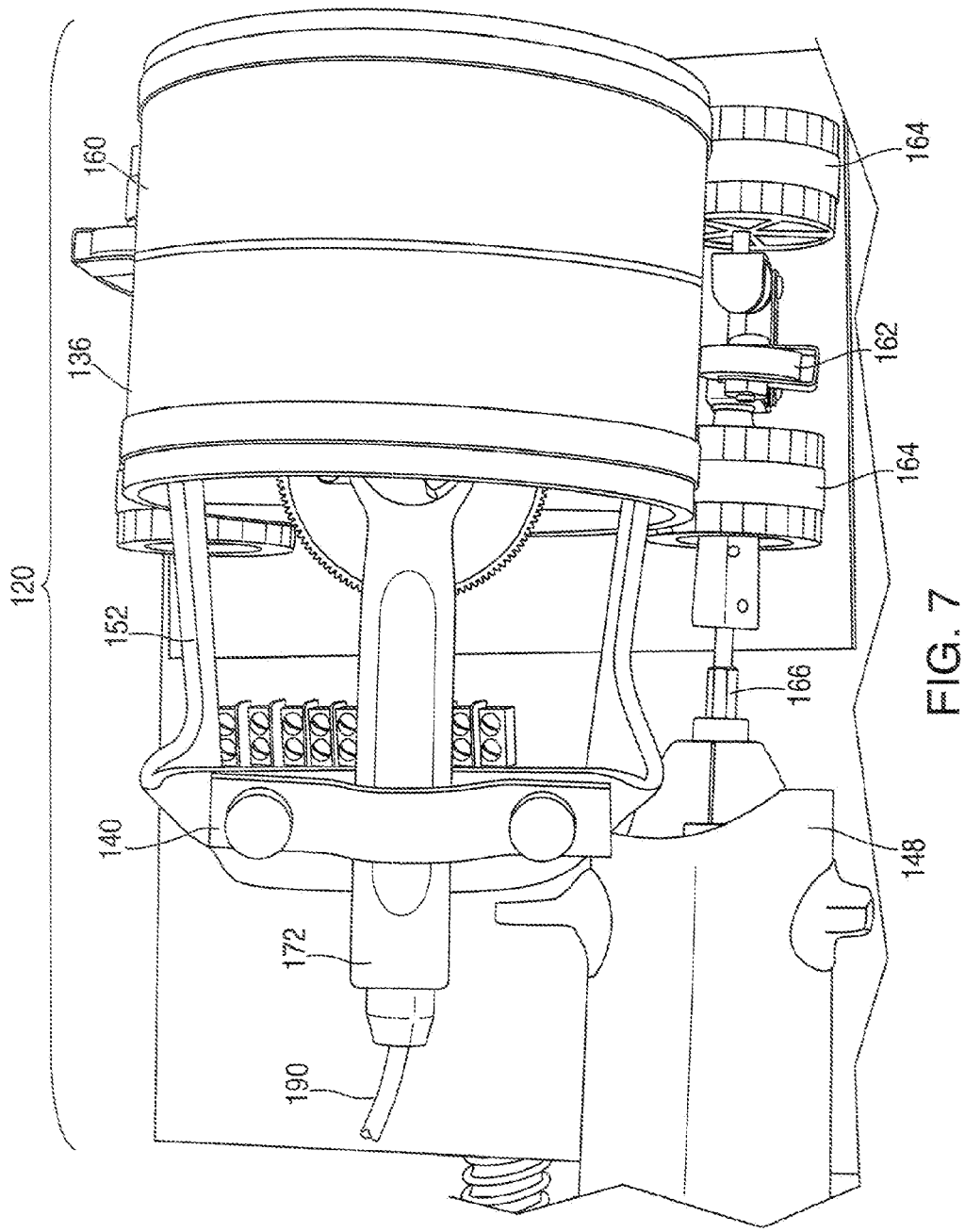
FIG. 7 is a top view of a handle controller in accordance with an embodiment of the invention.

The structure of the handle controller 120 is described in greater detail in FIGS. 5, 6 and 7. Handle controller 120 comprises a housing 134 (shown in an open position in FIG. 5) and a support base 114. Mounted to support base 114 is a rotation assembly 152, a motor 148 and terminal connectors 146. As with terminal connectors 108, terminal connectors 146 facilitate engagement of wires 126 with motor 148. A detachable handle 136 is shown attached to rotation assembly 152. Disposed within handle 136 is catheter 142 (FIG. 1).

It is a significant feature of the invention that commercially available, off the shelf catheters can be used. As handle 136 is detachable from rotation assembly 152, different handles may be used for different types of catheters 142. In the example shown in the FIG. 1, a BLAZER II XP™ cardiac ablation catheter (available from Boston Scientific Corporation, Natick, Mass.) with a corresponding handle 136 is used. Clearly other handles and catheters could be used. For example, a SAFIRE™ bi-directional ablation catheter (available from St. Jude Medical, St. Paul, Minn.) may be used along with a corresponding handle 136. Similarly, an RF MARINR®, RF CONTRACTR®, or RF CONDUCTR® ablation catheter (available from Medtronic, Inc., Minneapolis, Minn.), might also be used similarly. A fastening mechanism 140 may attach catheter 142 to handle 136.

Rotation assembly 152 includes drive wheels 164, driven wheels 150, support wheels 162, and a grooved support wheel 139. Motor 148 imparts rotation to drive wheels 164 to rotate handle 136. Driven wheels 150 support and facilitate rotation of handle 136. Handle 136 includes a hollowed cylinder 160 whose circumference engages with drive wheels 164, driven wheels 150 and support wheels 162. A radial edge of cylinder 160 mates with grooved support wheel 139. In use, catheter 142 is inserted into the hollow portion of cylinder 160 and is mounted to handle 136 using fastening mechanism 140 including a clamp base 154 and a clamp 156. Clamp 156 is connected to clamp base 154 with screws 158.

As shown in FIG. 7, upon actuation of motor 148, axis 166 rotates, causing drive wheels 164 to rotate. The rotation of drive wheels 164 imparts rotation of cylinder 160 supported by support wheels 162 and driven wheels 150. Catheter 142 is disposed within cylinder 160 and retained there through the use of fastening mechanism 140. In this way, by actuating motor 148, handle 136 can be caused to rotate either clockwise or counterclockwise. A slip connector (not shown) may be applied at the end of handle 136 so that wires 190 of catheter 142 are free to rotate. A sensor (not shown) may be disposed proximate to motor 148 or any part of rotation assembly 152 to sense a rotation of handle 136.

Figure 8:
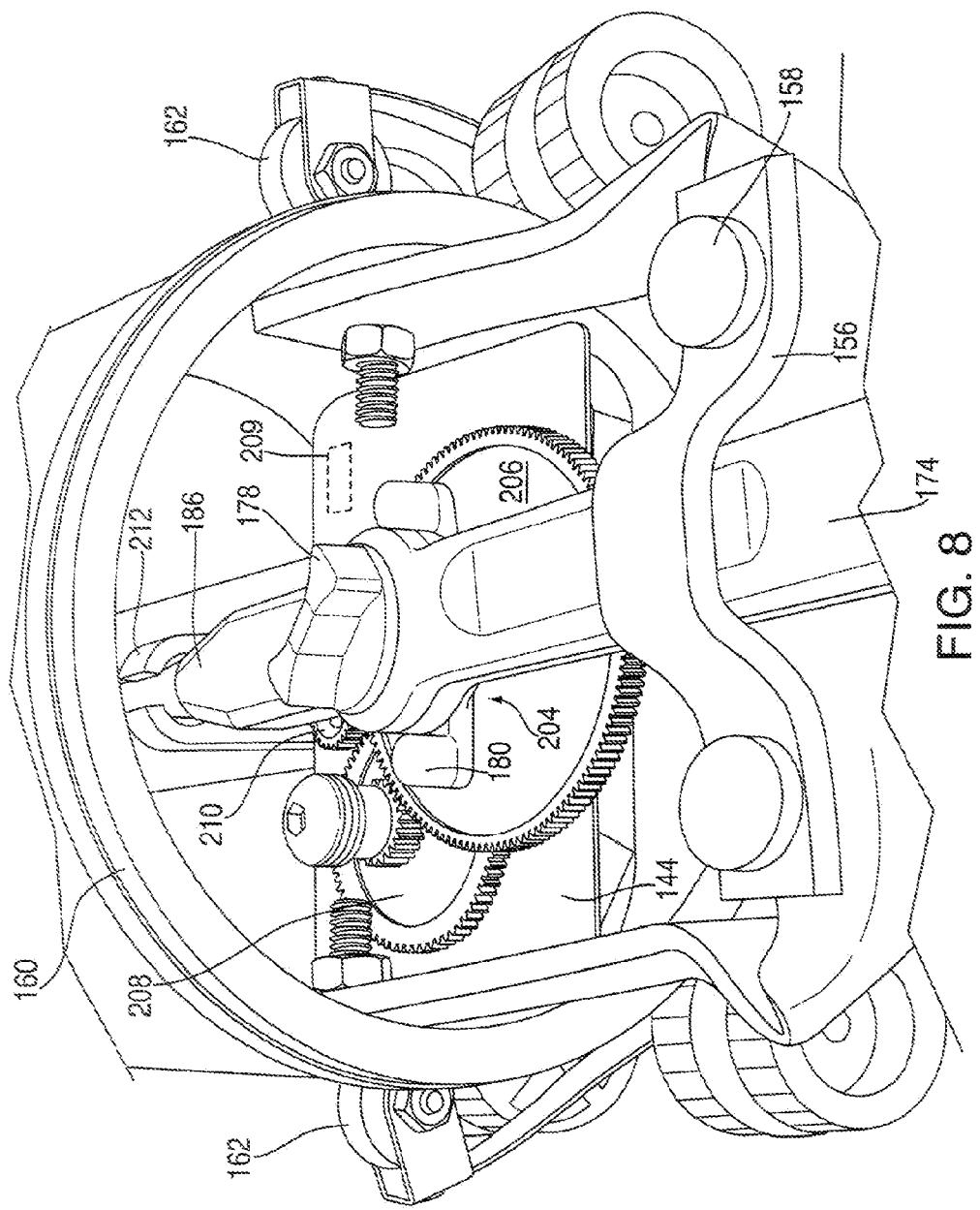
FIG. 8 is a lateral perspective view of a handle controller in accordance with an embodiment of the invention.
Figure 9:
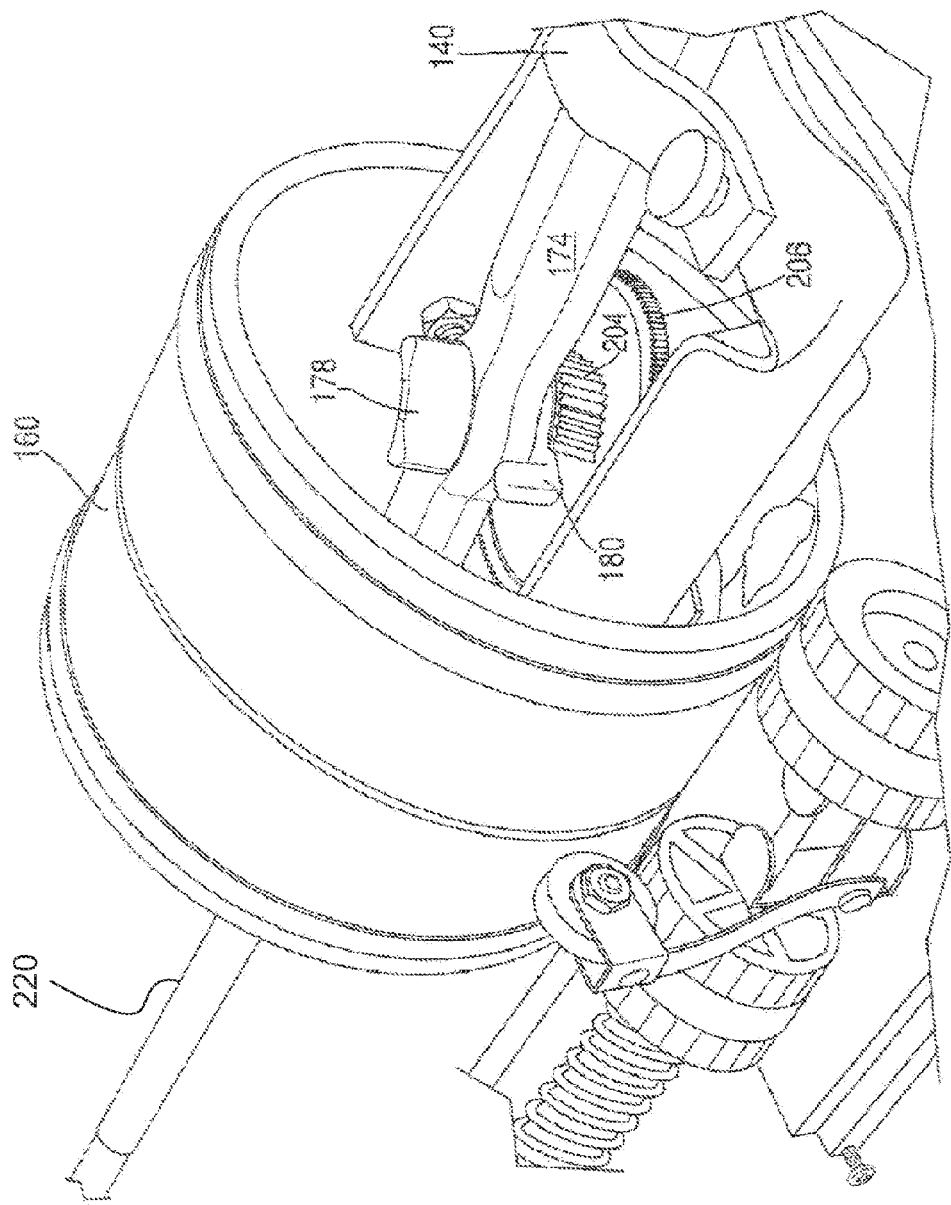
FIG. 9 is a lateral perspective view of a handle controller in accordance with an embodiment of the invention.

A structure for controlling deflection of a catheter end is shown in FIGS. 8 and 9. A portion of handle controller 120 is capable of accomplishing deflection of distal end 188 of catheter 142 (FIG. 1). A motor 209 disposed on an underside of a support base 144, imparts rotation to a driving gear 210. Driving gear 210 meshes with a first driven gear 208. First driven gear has an extension which, in turn, meshes with second driven gear 206. Second driven gear 206 has a gear extension 204 extending upwardly therefrom. Gear extension 204 defines an opening for placement of knob 180 of grip 176 of catheter 142. Due to the opening defined by gear extension 204, rotation of gear 206 imparts rotation to gear extension 204 which, in turn, imparts rotation to knob 180. Therefore, upon a rotation of motor 209, rotation is imparted to driving gear 210, first driven gear 208, second driven gear 206, gear extension 204, and knob 180. Such movement causes deflection of distal end 188 of catheter 142 (shown in FIG. 1). A sensor (not shown) may be installed proximate to motor 209 or to any one of gears 206, 208 or 210 so as to measure a rotation of said gears and thereby measure or suggest imparted deflection on distal end 188.

Catheter 142 is installed into handle 136 at three locations. Knob 180 is inserted into the space defined by gear extension 204 as discussed above. As discussed with reference to FIG. 6, proximal end 174 of catheter 172 is mounted to handle 136 mechanism 140 through the use of clamp 156. Additionally, proximal end 186 of catheter 172 is snap-fit into a stabilizer bar as can be seen in FIGS. 5, 8, 10 and 11. If catheter 142 has an additional range of motion, such as the point of deflection in a Medtronic ablation catheter, an additional motor can be attached to move the corresponding control on the handle.

Figure 10:
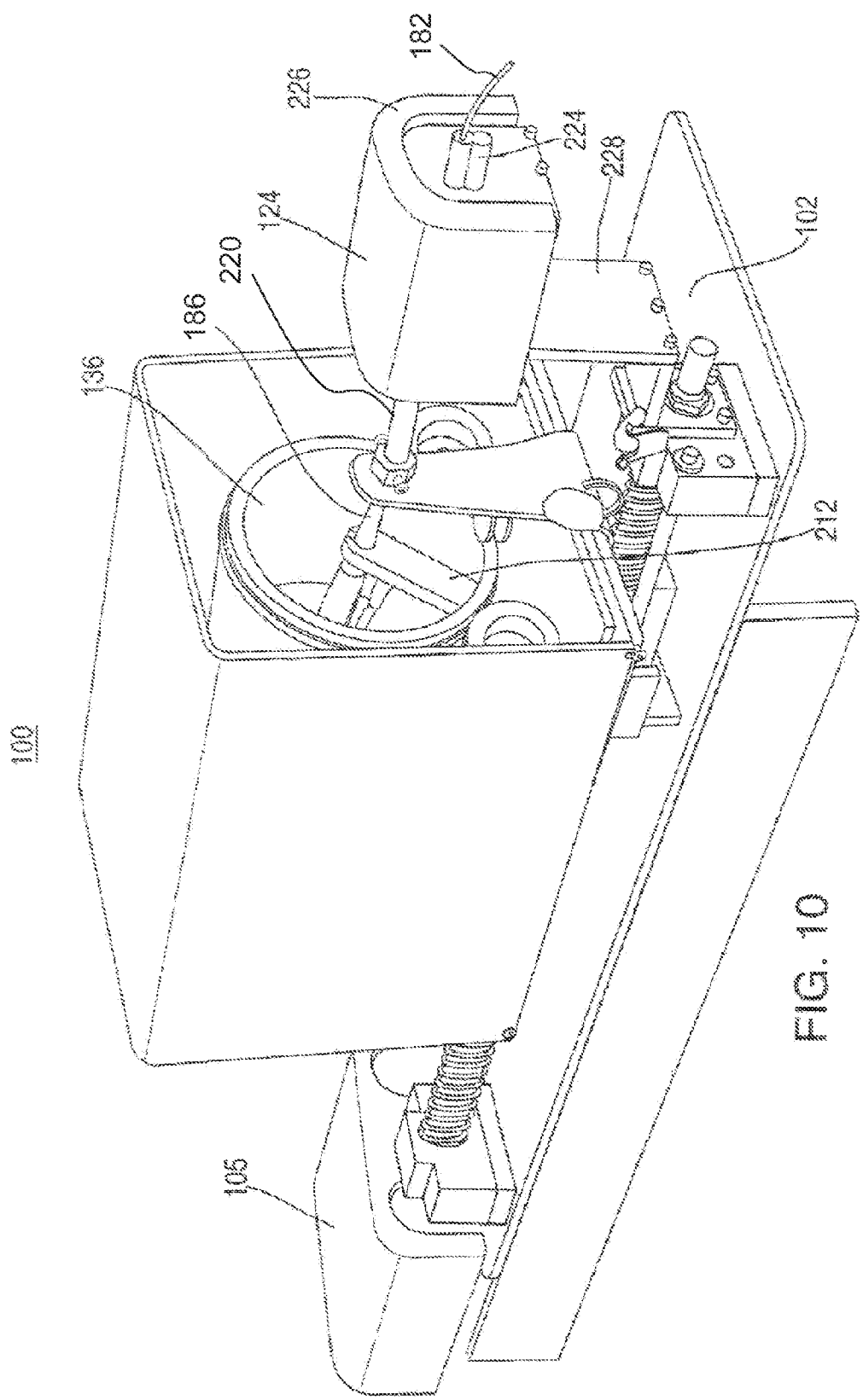
FIG. 10 is a lateral perspective view of a remotely controlled catheter insertion system in accordance with an embodiment of the invention.
Figure 11:
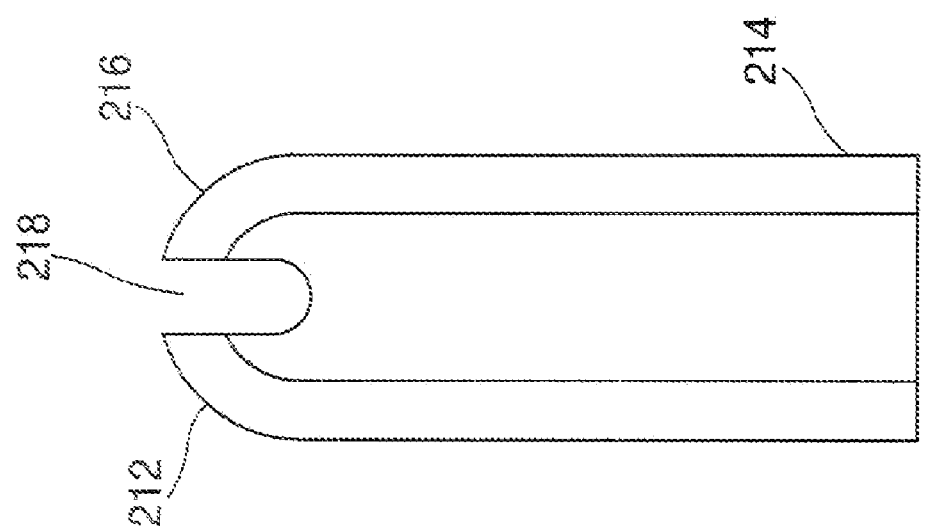
FIG. 11 is a lateral view of a stabilizer bar in accordance with an embodiment of the invention.

With reference to FIGS. 10 and 11 stabilizer bar 212 includes a base 214 and a top portion 216 defining in an opening 218. Opening 218 is designed to be large enough to just fit flexible catheter sheath 182 of catheter 142 in a snap fit arrangement. As shown in for example, FIG. 10, stabilizer bar 212 is mounted to an inner side of handle 136 and is effective to stabilize catheter 142 mounted therein. Moreover, stabilizer bar 212 may be used to absorb excessive forward and backward motion imparted to catheter 142. For example, if catheter 142 is pushed forward too aggressively or too quickly, opening 218 of bar 212 will slide along a circumference of flexible portion 186. Similarly, a sensor (not explicitly shown) may be installed within stabilizer bar 212 so as to measure an amount of forward or backward force being imparted on to catheter 172. A limiter may be connected to the motor and used to limit an amount of forward or backward force based on recordings by the sensor.

Figure 12:
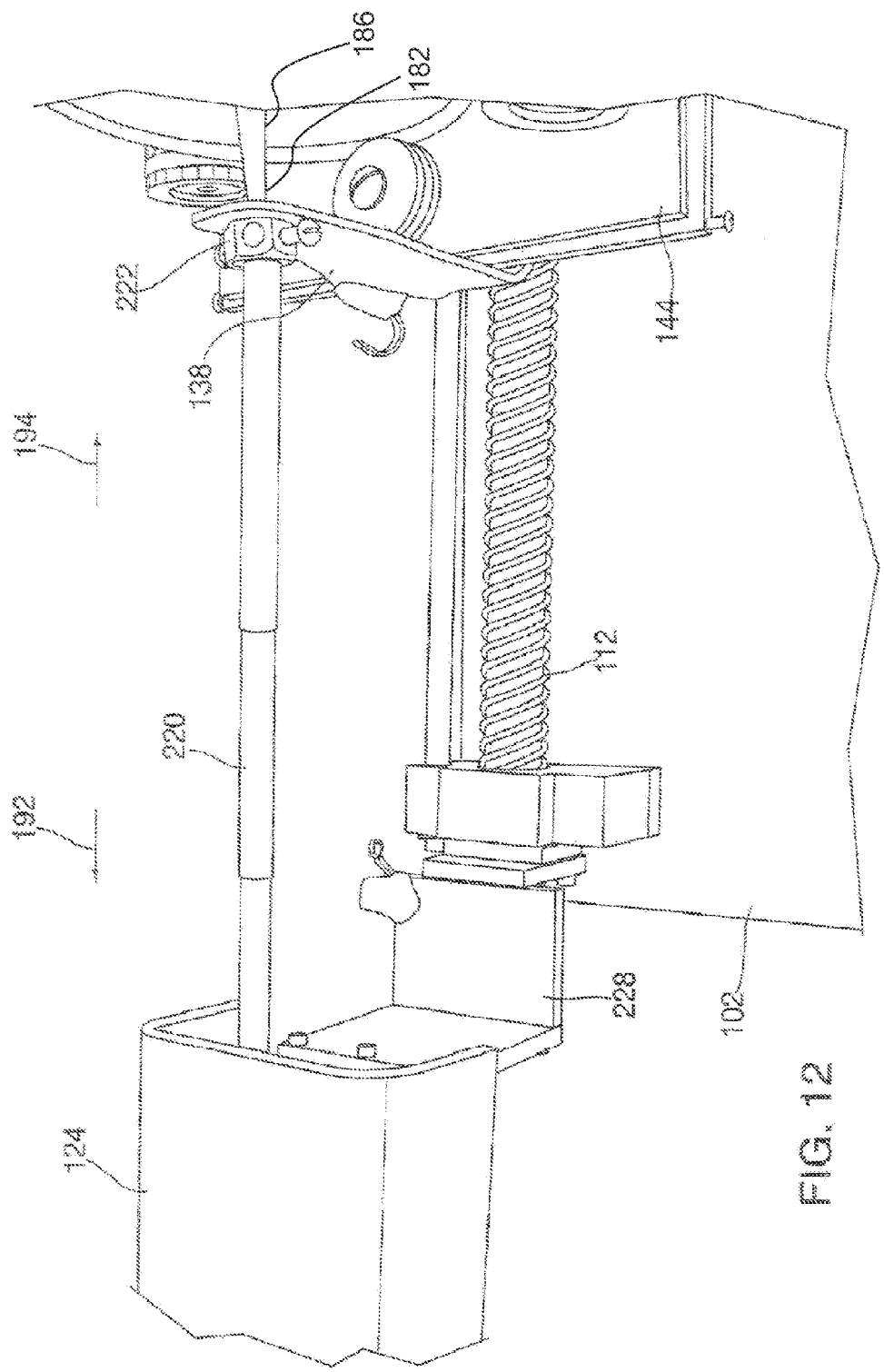
FIG. 12 is a top perspective view of a telescoping rod in accordance with an embodiment of the invention.

Catheter sheath 182 is very flexible. Such flexibility means that if too much force is applied to catheter sheath 182, catheter sheath 182 may buckle instead of moving forward into a patient. System 100 has various mechanical devices to avoid such buckling. Referring to FIG. 12, after flexible catheter sheath 182 is inserted into stabilizer bar 212, catheter sheath 182 is inserted into guide 138. Catheter sheath 182 is further inserted into a telescoping rod 220. As handle controller 120 (FIG. 2) moves forward and backward in directions 192 and 194, catheter sheath 182 moves internal to telescoping rod 220. Moreover, as telescoping rod 220 is fixed to an end of support base 144 of handle controller 120 through a fastening mechanism 222, movement of handle controller 120 generates the telescoping action of telescoping rod 220. That is, telescoping rod 220 contracts or expands based on forward/backward movement of handle controller 120. Telescoping rod 220 may be disposed of, or sterilized after every use of catheter 172 by disengagement of fastening mechanism 222. Telescoping rod 220 may be a collapsible tube constructed of interlocking cylinders (or cones) of smaller size, whose inner diameter easily fits and delivers a catheter, lead, or medical device without significant resistance. It is much like a collapsible cup or an antenna. This embodiment of the invention can allow the controller to deliver the catheter, lead, and/or medical device almost in it's entirety into the human body.

Figure 13:
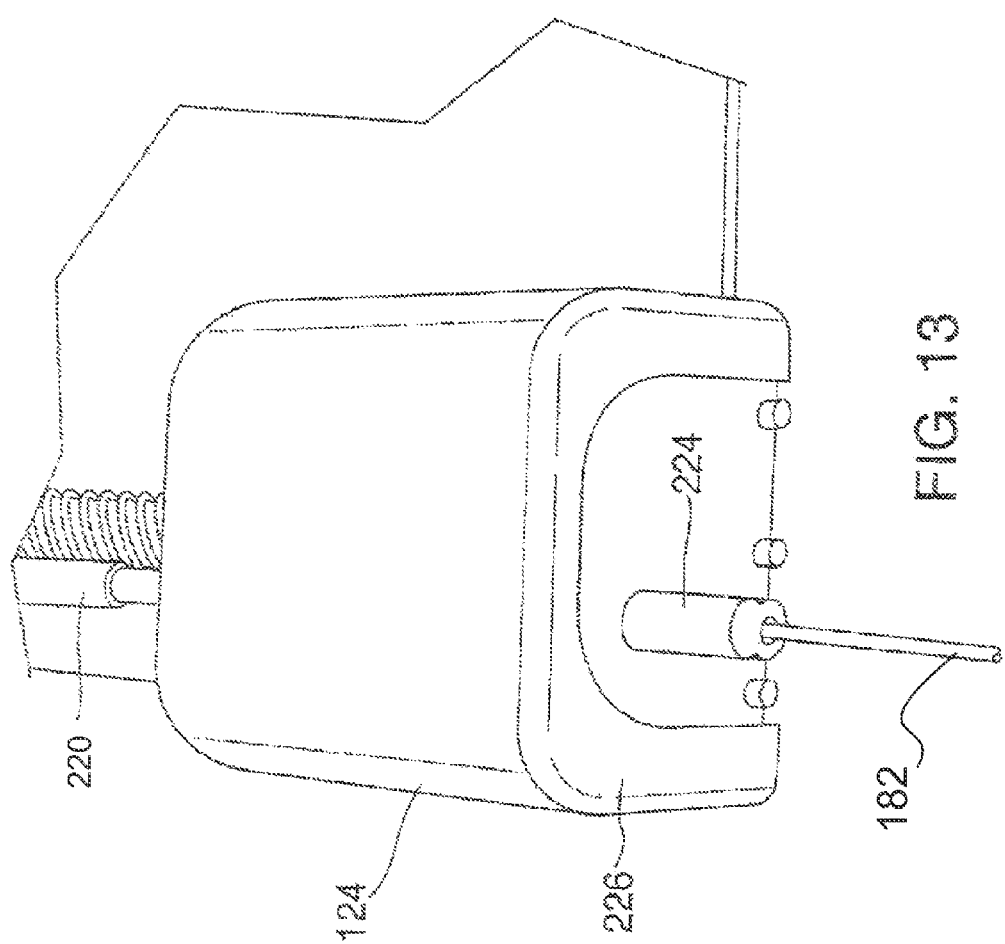
FIG. 13 is a side perspective view of a remotely controlled catheter insertion device in accordance with an embodiment of the invention.

To further assist in the feeding of catheter sheath 182 and to avoid buckling of the same, a catheter feeder 124 is used. Referring to FIGS. 10, 12 and 13, an end of telescoping rod 220 terminates at catheter feeder 124 and includes a housing 226 and a clip portion 224. As discussed previously, catheter sheath 182 is inserted internally to telescoping rod 220. Catheter sheath 182 exits from catheter feeder 124 through clip 224. Clip 224 is an external device which attaches the outside part of catheter feeder 124 directly to an introducer sheath (not shown) to maintain a fixed and precise distance (i.e., close proximity) to catheter sheath 182 and provide further protection against buckling of catheter sheath 182. If desired, an introducer sheath may be affixed to an end of clip 224 so that catheter sheath 182 exits catheter feeder 124 immediately into the introducer. Catheter feeder 124 is mounted to base 102 of system 100 through bracket 228.

Referring again to FIG. 1, as discussed, catheter 142 is capable of being manipulated in six ranges of motion: forward and backward 192, 194, rotation clockwise and counterclockwise 196 and 198, and deflection of a distal tip to positions 188*a* and 188*b*. In system 100, the movement forward and backward 192, 194 is controlled through the use of motor 105 and the engagement of drive screw 112 with drive support 118—as can be seen most clearly in FIGS. 2 and 3. Clockwise and counter-clockwise rotation 196 and 198 is effectuated through the use of motor 148 imparting motion through drive wheels 164 and cylinder 160—as can be seen most clearly in FIG. 7. The deflection of distal end 188 towards positions 188*a* and 188*b* is effectuated through the use of motor 209 and the engagement of gears to 210, 208 and 206—as is shown in FIG. 8. Thus, three motors operable in two directions each, provide control for the six ranges of motion. It is within the scope of the invention that additional motors may be present to provide additional catheter movement.

Figure 14:
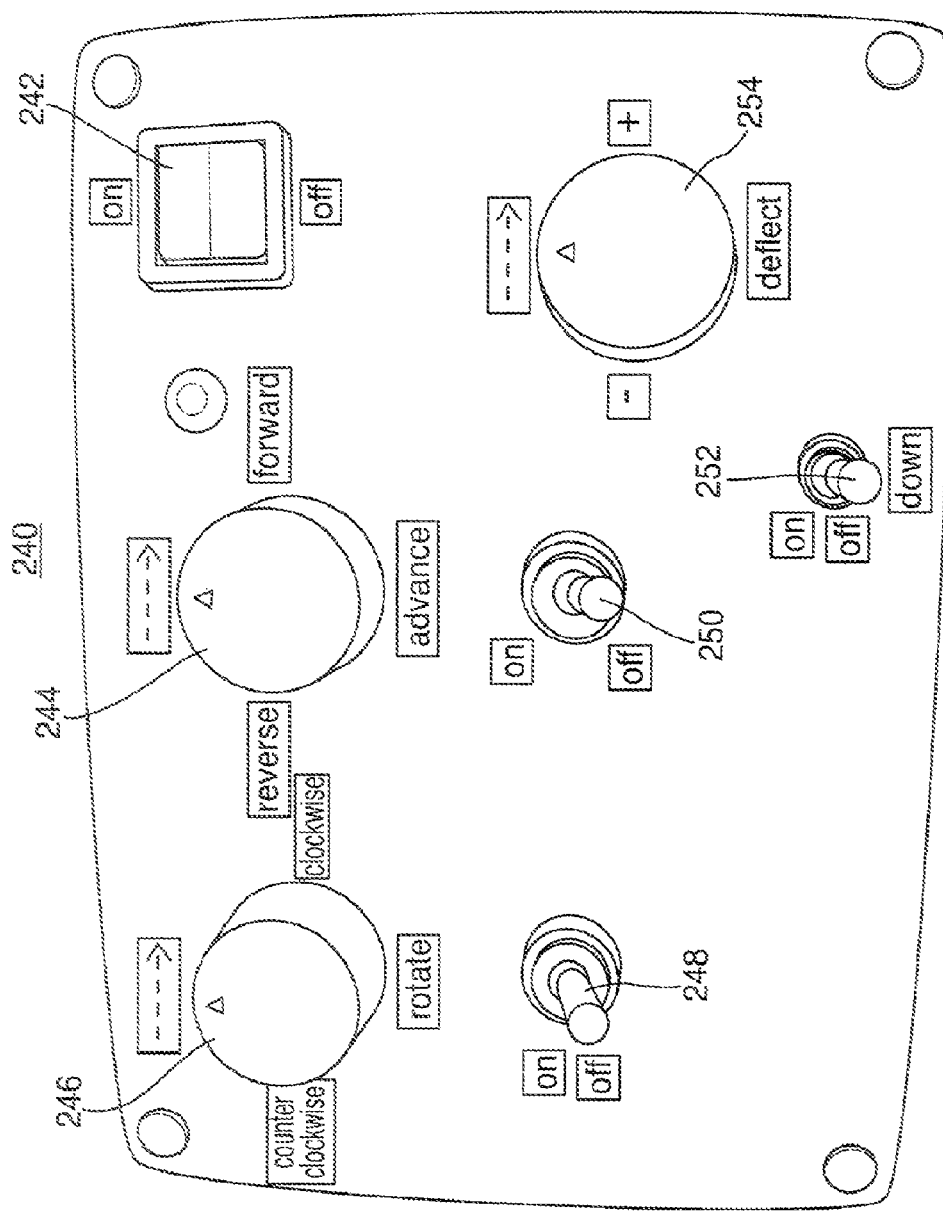
FIG. 14 is a top view of a controller in accordance with an embodiment of the invention.

Referring to FIG. 14, there is shown a remote control station 240 which could be used in accordance with an embodiment of the invention. Remote control station 240 has a master switch 242 effective to supply power to each of the motors connected to remote control station 240. A forward/reverse dial 244 is connected to motor 105 (FIG. 2) so that movement of dial 244 supplies power and a control signal to motor 105 and imparts forward and backward movement of catheter 142. A forward/reverse power switch 250 selectively supplies power to dial 244. A rotation dial 246 is connected to motor 148 (see FIG. 7) so that movement of dial 246 supplies power and a control signal to the motor and causes rotational movement of catheter 142. A rotation power switch 248 selectively supplies power to dial 246. A deflection dial 254 is connected to motor 209 (see FIG. 8). Movement of dial 244 supplies power and control signals to motor 209 and imparts deflection of distal end 188 of catheter 142. A deflection power switch 252 selectively supplies power to dial 254. In this way, all of the ranges of movement of catheter 142 can be controlled through the use of remote control 240. If the catheter has wires attached to it for electricity, heating or cooling such wires may also be connected to control station 240. Dials may be used to generate on/off signals or analog signals corresponding to various speeds for the motors.

Figure 15:
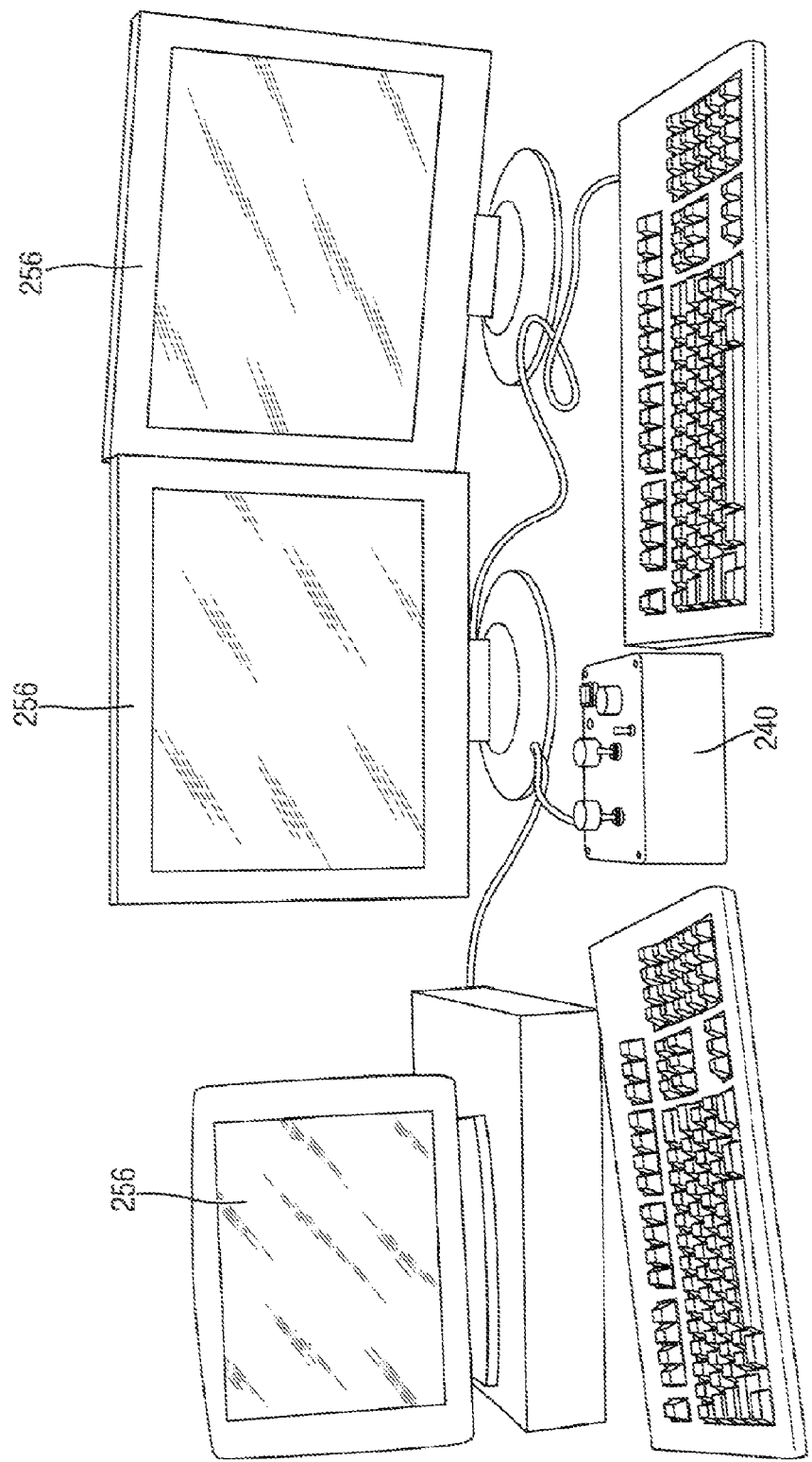
FIG. 15 is a front view of a system layout in accordance with an embodiment of the invention.

Referring now to FIG. 15, remote control station 240 can be disposed at a location which is spaced from the rest of system 100. For example, a technician or doctor operating system 100 may control catheter 142 remotely through the use of remote control station 240. Remote control station 240 may even be in a separate room from the rest of system 100. A technician may be able to view screens 256 supplying information regarding a procedure (such as fluoroscopy) while operating control station 240. Control station 240 can be connected to system 100 in a variety of means including wires and/or wireless connections. It is within the scope of the invention that the system described herein may be operated simultaneously or in conjunction with other mapping and/or visualization systems. Such other systems include a CARTO® (available from Biosense Webster, Inc., Diamond Bar, Calif.) or EnSite™ (available from Endocardial Solutions Inc., St. Paul, Minn.) mapping system or conventional infrared or ultrasound visualization systems.

Thus, by utilizing conventional, commercially available catheters, a more adaptable and inexpensive remotely controlled catheter insertion system is realized. As standard catheters are used, and catheters are the only instruments which would be inserted into a subject, no additional governmental approval may be needed. As a modular handle is used, catheters of various sizes, shapes and manufacturers can all be incorporated into the system. The use of the telescoping rod means that the system is more sterile as the rod may be easily designed to be disposable. In addition, the motor activated to feed the catheter into the body may be eliminated, and catheter stability, synchronization, and control may be improved. Technicians can easily adapt to use of the controller as familiar controls and screens are available and viewed by the technician.

The described system is comparatively safe due to the provision of many features. For example, the motor effective to move a catheter forward and backward may ultimately apply less force than is available through a human hand and therefore there is less concern for perforation. Such force can be sensed through various sensors so as to ensure that excessive force is not applied such as through the stabilizer bar. Similarly, sensors can be applied to detect the amount of clockwise and counter-clockwise movement and movement of the gears facilitating deflection of the distal end of the catheter. Use of all this sensor data helps ensure a safe system. In addition, certain limits, cut-offs, etc., could provide a level of safety even beyond that of a manually performed procedure.

Clearly any type of catheter could be used such as a diagnostic catheter or angiographic catheter, or catheters including various types of pumps, stylettes, guide-wires or balloons. Positions of the catheter may be maintained even if power is shut off. For example, all six ranges of motion are not dependent upon continuous power supply. The amount of forward or backward movement, rotation and deflection are all not dependent on a continuous supply of power. For example, a particular deflection may be set and then the deflection motor may be turned off while the rotation motor is applied. Similarly, a continuous radiofrequency ablation treatment may be implemented for a particular deflection angle while the catheter is remotely pulled back to create a linear ablation. Some types of treatments include microwave, ultrasound, radiofrequency, cryoablation, chemical ablation, delivery of biologics, etc. Conventional non-fluoroscopic three-dimensional mapping can be used to track catheter movement and ablation applications.

While prior art controllers required a user to learn a new control scheme, the invention relies on control schemes known by users and generally taught in school.

The position of the catheter can be measured and recorded using fluoroscopy and/or 3D mapping systems. Using a computer program and feedback system the robotic device could automatically or semi-automatically manipulate the catheter to position and place the catheter according to the operator's specifications. Software programs using feedback from the catheter system with appropriate fail-safes could manipulate and perform catheter ablations in precise targeted locations without the operator necessarily remotely moving the catheter. The operator could monitor the automatic and targeted operations and could shut off the system if there is any deviation from a planned and targeted mapping/ablation procedure. For example, a software program can analyze, through the sensors, the movements of each of the motors and/or gears for particular placement of a catheter inside a subject. As an example, a technician may first perform a procedure while software is analyzing the movements of each of the motors. Thereafter the software may be used as supplement to the control station so as to robotically control a catheter to a particular location and/or perform a particular procedure. Such a function is particularly helpful in situations where certain procedures need to be repeated multiple times. In addition, the computer software could perform a series of iterative movements of the catheter towards a three-dimensional target, eventually focusing in on the target. The software program can learn from said movements and return to certain locations, and perform a series of maneuvers (possibly drawn or targeted on a computer) such as encircling pulmonary veins with ablation applications to achieve pulmonary vein isolation. In addition, cavo-tricuspid isthmus lines can be created to ablate atrial flutter. Finally, scar maps can be created and ablation lines automatically or semi-automatically formed to prevent reentrant ventricular tachycardia from occurring.

The systems as described can be disposed anywhere including being mounted by a boom off of, for example, a ceiling, mounted on a table, or on the side or across from a subject. The systems may be mounted and secured firmly to an insertion site so as to be able to translate insertion force without being moved backward.

Further, additional backend modules can remotely control manipulation, such as forward/backward, rotation, deflection, drug/contrast delivery, balloon inflation, energy/therapy delivery, or stent/device deployment.

While preferred embodiments have been described, the invention is only limited by the scope of the claims.

Those skilled in the art will recognize that the method and system of the present invention has many applications, may be implemented in many manners and, as such, is not to be limited by the preceding and following exemplary embodiments and examples. Additionally, the functionality of the components of the preceding and following embodiments may be implemented in different manners. Further, it is to be understood that the steps in the embodiments may be performed in any suitable order, combined into fewer steps or divided into more steps. Thus, the scope of the present invention covers conventionally known and future developed variations and modifications to the system components described herein, as would be understood by those skilled in the art.

What is claimed is:

1. A system, comprising:
    a catheter insertion system configured to position and control a catheter within the body of a patient, wherein the catheter has a catheter handle portion and wherein the catheter insertion system is securely affixed to a base or support; and
    a remote control mechanism configured to control the catheter insertion system,
    wherein the catheter insertion system comprises a handle controller coupled to a support base and adapted to engage the catheter handle portion, the handle controller comprising:
        a fastening mechanism;
        a handle assembly; and
        a catheter deflection control structure configured to engage a knob on the catheter handle portion when the catheter handle portion is inserted in the handle controller,
    wherein the handle controller is coupled to a telescoping rod so that when the catheter handle portion is inserted into the handle controller, a distal end of the catheter is inserted into and through the telescoping rod, and
    wherein a first end of the telescoping rod is fixed to an end of the support base of the handle controller through the fastening mechanism and a second end of the telescoping rod terminates at a catheter feeder that is secured to the base or support of the catheter insertion system such that as the handle controller moves forward and backward, the telescoping rod contracts and expands.

2. The system of claim 1, wherein the telescoping rod extends from the handle controller to the catheter feeder.

3. The system of claim 2, wherein the catheter feeder includes a clip effective to inhibit buckling of the catheter.

4. The system of claim 1, wherein the telescoping rod is a collapsible tube with an inner diameter sized to deliver a medical device such as a catheter or lead without buckling.

5. The system of claim 1, wherein the telescoping rod is constructed of interlocking cylinders such that as the cylinders get closer to the handle controller they get progressively larger.

6. The system of claim 1, wherein the telescoping rod is constructed of interlocking cylinders of smaller size such that as the handle controller is moved closer to the catheter feeder, the interlocking cylinders collapse within each other.

7. The system of claim 1, where in the telescoping rod is disposable.

8. The system of claim 1, where in the telescoping rod is sterilizable.

* * * * *